(12) United States Patent
Liu et al.

(10) Patent No.: US 11,020,454 B2
(45) Date of Patent: Jun. 1, 2021

(54) FUSION POLYPEPTIDES AND METHODS OF USE

(71) Applicant: PROSIT SOLE BIOTECHNOLOGY (BEIJING) CO., LTD, Beijing (CN)

(72) Inventors: Hongyu Liu, Beijing (CN); Mingzhi Zhao, Beijing (CN); Hetong Sun, Beijing (CN)

(73) Assignee: PROSIT SOLE BIOTECHNOLOGY (BEIJING) CO. LTD, Beijing (CN)

( * ) Notice: Subject to any disclaimer, the term of this patent is extended or adjusted under 35 U.S.C. 154(b) by 0 days.

(21) Appl. No.: 15/744,712

(22) PCT Filed: Jul. 15, 2016

(86) PCT No.: PCT/CN2016/090110
§ 371 (c)(1),
(2) Date: Jan. 12, 2018

(87) PCT Pub. No.: WO2017/008758
PCT Pub. Date: Jan. 19, 2017

(65) Prior Publication Data
US 2018/0200333 A1      Jul. 19, 2018

(30) Foreign Application Priority Data
Jul. 15, 2015 (WO) ................ PCT/CN2015/084133

(51) Int. Cl.
| | | |
|---|---|---|
| A61K 38/18 | (2006.01) | |
| C07K 14/50 | (2006.01) | |
| A61P 19/08 | (2006.01) | |
| A61K 38/00 | (2006.01) | |
| C12N 15/10 | (2006.01) | |
| C12N 15/62 | (2006.01) | |
| C12N 15/74 | (2006.01) | |

(52) U.S. Cl.
CPC .............. *A61K 38/18* (2013.01); *A61P 19/08* (2018.01); *C07K 14/50* (2013.01); *C12N 15/10* (2013.01); *C12N 15/62* (2013.01); *C12N 15/74* (2013.01); *A61K 38/00* (2013.01); *C07K 2319/00* (2013.01); *C12N 2510/02* (2013.01)

(58) Field of Classification Search
None
See application file for complete search history.

(56) References Cited

U.S. PATENT DOCUMENTS

| | | | |
|---|---|---|---|
| 4,500,707 A | 2/1985 | Caruthers et al. | |
| 5,436,327 A | 7/1995 | Southern et al. | |
| 5,700,637 A | 12/1997 | Southern | |
| 6,368,822 B1 * | 4/2002 | Greene .................. | C07K 14/50 435/320.1 |
| 7,288,406 B2 * | 10/2007 | Bogin ..................... | C07K 14/50 435/320.1 |
| 7,414,019 B2 * | 8/2008 | Cornish ............... | A61K 38/1825 514/1.1 |
| 7,470,665 B2 * | 12/2008 | West ....................... | C07K 16/46 514/1.1 |
| 7,858,341 B2 | 12/2010 | Reardon et al. | |
| 9,226,949 B2 * | 1/2016 | Yayon ................. | A61K 38/1825 |
| 2009/0286728 A1 | 11/2009 | Ota et al. | |
| 2010/0286042 A1 | 11/2010 | Imamura et al. | |

FOREIGN PATENT DOCUMENTS

| | | |
|---|---|---|
| CN | 1247568 A | 3/2000 |
| CN | 101505787 A | 8/2009 |
| CN | 102656266 A | 9/2012 |
| EP | 2213296 A1 | 8/2010 |
| JP | 2010501531 A | 1/2010 |
| JP | 2013507930 A | 3/2013 |
| JP | 2014527402 A | 10/2014 |
| WO | WO-9852976 A1 | 11/1998 |
| WO | WO-0003317 A1 | 1/2000 |
| WO | WO-02079232 A2 | 10/2002 |
| WO | WO-2007099953 A1 | 9/2007 |
| WO | WO-2008023063 A2 | 2/2008 |
| WO | WO-2009048119 A1 | 4/2009 |
| WO | WO-2011047267 A1 | 4/2011 |
| WO | WO-2013006486 A2 | 1/2013 |
| WO | WO-2017008758 A1 | 1/2017 |

OTHER PUBLICATIONS

Ohbayashi et al., Journal of Biological Chemistry, vol. 273, No. 29, p. 18161-18164, 1998.*
Zhang et al., Journal of Biological Chemistry, vol. 281, No. 23, p. 15694-15700, 2006.*
Beenken, et al., The FGF family: biology, pathophysiology and therapy. Nat Rev Drug Discov. Mar. 2009;8(3):235-53. doi: 10.1038/nrd2792.
Buckwalter, J.A. et al., The impact of osteoarthritis: implications for research. Clin Orthop Relat Res. Oct. 2004;(427 Suppl):S6-15.
Cespedes, et al. Mouse models in oncogenesis and cancer therapy. Clin Transl Oncol. May 2006;8(5):318-29.
Ekenstedt, KJ. Effects of Chronic growth hormone and insulin-like growth factor 1 deficiency on osteoarthritis severity in Rat knee joints. Arthritis Rheum. 2006; 54:3850-3858.
Ellman, et al., Biological impact of the fibroblast growth factor family on articular cartilage and intervertebral disc homeostasis: basic FGF, FGF-18, osteoarthritis, IVD degeneration. Gene. Aug. 2008; 420(1):82-89.

(Continued)

*Primary Examiner* — Marianne P Allen
(74) *Attorney, Agent, or Firm* — Wilson Sonsini Goodrich & Rosati

(57) ABSTRACT

Provided are fusion polypeptides comprising fragments from a first and a second FGF family member, nucleic acids encoding the fusion polypeptides, vectors and host cells containing the same, and methods of making and using such compositions in the treatment of FGF-related diseases, disorders, and conditions.

9 Claims, 11 Drawing Sheets
Specification includes a Sequence Listing.

(56) References Cited

OTHER PUBLICATIONS

EMBOSS. EMBOSS Needle: Pairwise Sequence Alignment (NUCLEOTIDE). Available at http://www.ebi.ac.uk/Tools/psa/emboss_needle/nucleotide.html. Accessed on Oct. 10, 2016.

Hopp, et al. Prediction of protein antigenic determinants from amino acid sequences. Proc Natl Acad Sci U S A 1981; 78, 3824-3828, #3232.

Kerbel, et al. Human tumor xenografts as predictive preclinical models for anticancer drug activity in humans: better than commonly perceived-but they can be improved. Cancer Biol Ther. Jul.-Aug. 2003;2(4 Suppl 1):S134-9.

Levitt, M. A simplified representation of protein conformations for rapid simulation of protein folding. Journal of Molecular Biology. Jun. 1976; 104(1): 59-107.

Man, et al. On the development of models in mice of advanced visceral metastatic disease for anti-cancer drug testing. Cancer Metastasis Rev. Dec. 2007;26(3-4):737-47.

Matteucci, et al. The synthesis of oligodeoxyprimidines on a polymer support. Tetrahedron Letters 21.8 (1980): 719-722. doi:10.1016/S0040-4039(00)71455-.

Needleman et al. A general method applicable to the search for similarities in the amino acid sequence of two proteins. J. Mol. Biol. 48:443-453 (1970).

PCT/CN2016/090110 International Search Report and Written Opinion dated Oct. 26, 2016.

Stickler, et al. Human population-based identification of CD4(+) T-cell peptide epitope determinants. J Immunol Methods. Oct. 1, 2003;281(1-2):95-108.

Sturniolo, T. et al., Generation of tissue-specific and promiscuous HLA ligand databases using DNA microarrays and virtual HLA class II matrices. Nat. Biotech. 17 (1999): 555-561.

Talmadge, et al. Murine models to evaluate novel and conventional therapeutic strategies for cancer. Am J Pathol. Mar. 2007;170(3):793-804.

European Search Report dated Jan. 22, 2019 for EP Application No. 16823905.1.

Imamura, et al., Physiological functions and underlying mechanisms of fibroblast growth factor (FGF) family members: recent findings and implications for their pharmacological application. Biol Pharm Bull. 2014;37(7):1081-9.

Motomura, et al., An FGF1:FGF2 chimeric growth factor exhibits universal FGF receptor specificity, enhanced stability and augmented activity useful for epithelial proliferation and radioprotection. Biochim Biophys Acta. Dec. 2008;1780(12):1432-40. doi: 10.1016/j.bbagen.2008.08.001. Epub Aug. 12, 2008.

Xu, et al. Genomic structure, mapping, activity and expression of fibroblast growth factor 17. Mechanisms of Development. vol. 83. Issues 1-2. May 1, 1999. pp. 165-178.

\* cited by examiner

|  | FGF1 | SEQ ID NO1 | SEQ ID NO2 | SEQ ID NO4 | SEQ ID NO 11 | SEQ ID NO 15 |
|---|---|---|---|---|---|---|
| EC50 | 5.292 | 20.09 | 19.38 | 18.35 | 4.896 | 30.48 |

FUSION POLYPEPTIDES AND METHODS OF USE

CROSS-REFERENCE

This application claims priority to PCT Application Serial No. PCT/CN2015/084133, filed Jul. 15, 2015, which application is herein incorporated by reference in their entireties for all purposes.

BACKGROUND

Fibroblast growth factor (FGF) 18, together with FGF8 and FGF17, represents a subset of the FGF family. They bind and signal through the FGFR family of tyrosine kinase receptors in a heparin sulfate glycosaminoglycan (HSGAG) dependent manner (Nature reviews drug discovery. 2009; vol 8:235-253).

FGF18 increases chondrocyte proliferation and stimulates extracellular matrix (ECM) formation in vitro and in injured but not normal joint in vivo (Arthritis Rheum. 2006; 54:3850-3858. Gene. 2008; 420:82-89.).

Osteoarthritis (OA) is a prevalent disease in the world with staggering socioeconomic effects on today's society. It is the leading cause of disability among the elderly population (Clin Orthop Relat Res 2004:S6-S15). The pathogenesis of this condition involves the progressive deterioration of cartilage tissue. Full thickness cartilage defects, including early OA, have limited healing potential. The use of FGF18 is under consideration as a potential therapy for cartilage repair and OA (Osteoarthritis and Cartilage 19S1 (2011) S7-S52). Current treatments including lifestyle changes, painkillers, and surgeries are of limited effects.

SUMMARY

As such, there is a considerable need for new drugs for OA as well as other diseases concerning cartilage repair. The present disclosure addresses such a need and provides related advantages as well. The present disclosure encompasses modified fusion polypeptides. The disclosure also provides methods for the production of the fusion polypeptides, such as in prokaryotic systems like $E.\ coli$. Further, the present disclosure provides pharmaceutical uses of the fusion polypeptides in the treatment of cartilage defects, including but not limited to osteoarthritis, degenerative disc disease and cartilage injury. In some embodiments, the present disclosure provides pharmaceutical uses of the fusion polypeptides in cartilage repair, e.g., in cartilage microfracture surgery.

In one aspect, the present disclosure provides a fusion polypeptide comprising a first fragment from a first member of a protein family and a second fragment from a second member of said protein family, wherein the first and second fragments are fused together at a fusion site to form a contiguous polypeptide. In some embodiments, the fusion site comprises a sequence of at least about 6 amino acids that is identical to a corresponding sequence in said first and said second member of said protein family.

The fusion polypeptide may have an ability to promote growth of cells expressing FGF receptors comparable to that of FGF18 (SEQ ID NO: 1) and/or FGF17 (SEQ ID NO: 2). In some embodiments, the cells express at least one FGF receptor selected from the group consisting of FGFR3, FGFR3c, FGFR3c-1c, FGFR3b, FGFR3-IIIc, FGFR3-IIIb, FGFR1c, FGFR2c, FGFR4-1c, and FGFRdelta4-1c. In some embodiments, the at least one FGF receptor is selected from the group consisting of FGFR3c and FGFR3c-1c. In some embodiments, the at least on FGF receptor is FGFR3c-1c. Further, the fusion polypeptide may have an ability to promote growth of the cells at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1). In some embodiments, the cells are BaF3 cells expressing the FGF receptors.

In some cases, the fusion polypeptide may have an ability to promote growth of BaF3 cells expressing the FGF receptor in vitro. Conversely, the fusion polypeptide may have an ability to promote growth of BaF3 cells expressing the FGF receptor in vivo. In some embodiments, the fusion polypeptide shows the ability to promote growth of BaF3 cells expressing the FGF receptor(s) in vitro when applied at a concentration of less than about 1 µg/ml, 100 ng/ml, 90 ng/ml, 80 ng/ml, 70 ng/ml, 60 ng/ml, 50 ng/ml, 40 ng/ml, 30 ng/ml, 29 ng/ml, 28 ng/ml, 27 ng/ml, 26 ng/ml, 25 ng/ml, 24 ng/ml, 23 ng/ml, 22 ng/ml, 21 ng/ml, 20 ng/ml, 19 ng/ml, 18 ng/ml, 17 ng/ml, 16 ng/ml, 15 ng/ml, 14 ng/ml, 13 ng/ml, 12 ng/ml, 11 ng/ml, 10 ng/ml, 9 ng/ml, 8 ng/ml, 7 ng/ml, 8 ng/ml, 5 ng/ml, 4 ng/ml, 3 ng/ml, 2 ng/ml, 1.5 ng/ml, 1 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, or 0.1 ng/ml. In some embodiments, the concentration applied may be 0.1 ng/ml to 100 ng/ml, e.g., 1 ng/ml to 100 ng/ml, 2 ng/ml to 100 ng/ml, 3 ng/ml to 100 ng/ml, 4 ng/ml to 100 ng/ml, 5 ng/ml to 100 ng/ml, 6 ng/ml to 100 ng/ml, 7 ng/ml to 100 ng/ml, 8 ng/ml to 100 ng/ml, 9 ng/ml to 100 ng/ml, 10 ng/ml to 100 ng/ml, 11 ng/ml to 100 ng/ml, 12 ng/ml to 100 ng/ml, 13 ng/ml to 100 ng/ml, 14 ng/ml to 100 ng/ml, 15 ng/ml to 100 ng/ml, 16 ng/ml to 100 ng/ml, 17 ng/ml to 100 ng/ml, 18 ng/ml to 100 ng/ml, 19 ng/ml to 100 ng/ml, 20 ng/ml to 100 ng/ml, 21 ng/ml to 100 ng/ml, 22 ng/ml to 100 ng/ml, 23 ng/ml to 100 ng/ml, 24 ng/ml to 100 ng/ml, 25 ng/ml to 100 ng/ml, 26 ng/ml to 100 ng/ml, 27 ng/ml to 100 ng/ml, 28 ng/ml to 100 ng/ml, 29 ng/ml to 100 ng/ml, 30 ng/ml to 100 ng/ml, 40 ng/ml to 100 ng/ml, 50 ng/ml to 100 ng/ml, 60 ng/ml to 100 ng/ml, 70 ng/ml to 100 ng/ml, 80 ng/ml to 100 ng/ml, or 90 ng/ml to 100 ng/ml.

In some embodiments, the fusion polypeptide has an ability to stimulate chondrocyte cell proliferation comparable to that of FGF18 (SEQ ID NO: 1) and/or FGF17 (SEQ ID NO: 2). For example, the fusion polypeptide may have an ability to stimulate chondrocyte cell proliferation at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1) and/or FGF17 (SEQ ID NO: 2). In some embodiments, the fusion polypeptide has an ability to stimulate chondrocyte cell proliferation at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1). In further cases, the fusion polypeptide may have an ability to stimulate chondrocyte cell proliferation at a level that is at least 50%, 60%, 70%, 80%, 90%, 100%, 150%, or 200%, of that of FGF18 (SEQ ID NO: 1).

In some embodiments, the fusion polypeptide has an ability to increase proteoglycan synthesis in chondrocyte cells comparable to that of FGF18 (SEQ ID NO: 1) and/or FGF17 (SEQ ID NO: 2). For example, the fusion polypeptide may have an ability to increase proteoglycan synthesis in chondrocyte cells at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1) and/or FGF17 (SEQ ID NO: 2). In some embodiments, the fusion polypeptide has an ability to increase proteoglycan synthesis in chondrocyte cells at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1). In further cases, the fusion polypeptide may have an ability to increase proteoglycan synthesis in chondrocyte cells at a level that is at least 50%, 60%, 70%, 80%, 90%, 100%, 150%, or 200%, of that of FGF18 (SEQ ID NO: 1).

In another aspect, the present disclosure provides a fusion polypeptide comprising a first fragment from a first member of FGF family and a second fragment from a second member of FGF family, wherein said first and second fragments are fused together at a fusion site to form a contiguous polypeptide. The fusion site may comprise a sequence of at least about 6 amino acids that is identical to a corresponding sequence in said first and said second member of the FGF family.

In some embodiments, the fusion polypeptide has an ability to promote growth of cells expressing FGF receptors, to stimulate chondrocyte cell proliferation, and/or to increase proteoglycan synthesis in chondrocyte cells comparable to that of FGF18 (SEQ ID NO: 1) and/or FGF17 (SEQ ID NO: 2). For example, the fusion polypeptide may have an ability to promote growth of cells expressing FGF receptors, to stimulate chondrocyte cell proliferation, and/or to increase proteoglycan synthesis in chondrocyte cells at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1) and/or FGF17 (SEQ ID NO: 2).

In some embodiments, the fusion polypeptide has an ability to promote growth of cells expressing FGF receptors, to stimulate chondrocyte cell proliferation, and/or to increase proteoglycan synthesis in chondrocyte cells at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1). For example, the fusion polypeptide may have an ability to promote growth of cells expressing FGF receptors, to stimulate chondrocyte cell proliferation, and/or to increase proteoglycan synthesis in chondrocyte cells at a level that is at least 50%, 60%, 70%, 80%, 90%, 100%, 150%, or 200% of that of FGF18 (SEQ ID NO: 1).

In some embodiments, the fusion polypeptide has an ability to promote growth of BaF3 cells expressing FGFR3c-1c at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1). For example, the fusion polypeptide may have an ability to promote growth of BaF3 cells expressing FGFR3c-1c at a level that is at least 50%, 60%, 70%, 80%, 90%, 100%, 150%, or 200% of that of FGF18 (SEQ ID NO: 1).

In some embodiments, the fusion polypeptide has an ability to promote growth of cells expressing FGF receptors, to stimulate chondrocyte cell proliferation, and/or to increase proteoglycan synthesis in chondrocyte cells at a level that is at least 20%, 30%, 40%, 50%, 60%, 70%, 80%, 90%, 100%, 150%, 200%, 250%, 300%, 350%, 400%, 450%, or 500% of that of FGF17 (SEQ ID NO: 2). For example, the fusion polypeptide may have an ability to promote growth of cells expressing FGF receptors, to stimulate chondrocyte cell proliferation, and/or to increase proteoglycan synthesis in chondrocyte cells at a level that is at least 50%, 60%, 70%, 80%, 90%, 100%, 150%, or 200% of that of FGF17 (SEQ ID NO: 2).

In some embodiments, the fusion polypeptide has an ability to promote growth of BaF3 cells expressing FGFR3c-1c at a level that is at least 20%, 30%, 40%, 50%, 60%, 70%, 80%, 90%, 100%, 150%, 200%, 250%, 300%, 350%, 400%, 450%, or 500% of that of FGF17 (SEQ ID NO: 2). For example, the fusion polypeptide may have an ability to promote growth of BaF3 cells expressing FGFR3c-1c at a level that is at least 50%, 60%, 70%, 80%, 90%, 100%, 150%, or 200% of that of FGF17 (SEQ ID NO: 2).

In some embodiments, the fusion polypeptide retains the secondary structure of said first or said second member.

In some embodiments, the fusion polypeptide is devoid of any additional T-epitope as compared to that of said first or said second member.

In some embodiments, the fusion polypeptide is devoid of any additional B-epitope as compared to that of said first or said second member.

In some embodiments, the protein family is FGF protein family.

In some embodiments, in the fusion polypeptide of the present disclosure, the first member is FGF18 or an isoform thereof.

In some embodiments, in the fusion polypeptide of the present disclosure, the second member is FGF17 or an isoform thereof.

In some embodiments, in the fusion polypeptide of the present disclosure, the first member is FGF18 or an isoform thereof and the second member is FGF17 or an isoform thereof.

In another aspect, the present disclosure provides a fusion polypeptide having a structure of formula (I):

(S1)-(β1)-(S2)-(β2)-(S3)-(β3)-(S4)-(β4)-(S5)-(β5)-(S6)-(β6)-(S7)-(β7)-(S8)-(β8)-(S9)-(β9)- (S10)-(β10)-(S11)-(β11)-(S12)-(β12)-S13     (I)

wherein:
a) β2 comprises an amino acid sequence exhibiting at least 90% homology to a fragment having residues from about I39 to G43 of FGF18 (SEQ ID NO:1) or from about V44 to G48 of FGF17 (SEQ ID NO:2);
b) β3 comprises an amino acid sequence exhibiting at least 90% homology to a fragment having residues from about R45 to A48 of FGF18 (SEQ ID NO:1) or from about R50 to A53 of FGF17 (SEQ ID NO:2);
c) β5 comprises an amino acid sequence exhibiting at least 90% homology to a fragment having residues from about Q69 to K75 of FGF18 (SEQ ID NO:1) or from about R74 to A80 of FGF17 (SEQ ID NO:2);
d) β6 comprises an amino acid sequence exhibiting at least 90% homology to a fragment having residues from about F79 to L81 of FGF18 (SEQ ID NO:1) or from about K84 to I86 of FGF17 (SEQ ID NO:2);
e) β7 comprises an amino acid sequence exhibiting at least 90% homology to a fragment having residues from about K88 to G91 of FGF18 (SEQ ID NO:1) or from about K93 to G96 of FGF17 (SEQ ID NO:2);
f) β8 comprises an amino acid sequence exhibiting at least 90% homology to a fragment having residues from about V101 to K105 of FGF18 (SEQ ID NO:1) or from about V106 to I110 of FGF17 (SEQ ID NO:2);
g) β10 comprises an amino acid sequence exhibiting at least 90% homology to a fragment having residues from about G121 to V124 of FGF18 (SEQ ID NO:1) or from about G126 to M129 of FGF17 (SEQ ID NO:2);
h) β11 comprises an amino acid sequence exhibiting at least 90% homology to a fragment having residues from about K134 to T138 of FGF18 (SEQ ID NO:1) or from about Q139 to S143 of FGF17 (SEQ ID NO:2);

each of S1, S2, S3, S4, S5, S6, S7, S8, S9, S10, S11, S12, and S13 is independently a spacer sequence having between 1 to about 50 amino acid residues;
and wherein:

i) β1 comprises an amino acid sequence exhibiting at least 90% homology to a fragment having residues from about Q24 to Y31 of FGF18 (SEQ ID NO:1); and β4 comprises an amino acid sequence exhibiting at least 90% homology to a fragment having residues from about K63 to T68 of FGF17 (SEQ ID NO:2); and β9 comprises an amino acid sequence exhibiting at least 90% homology to a fragment having residues from about Y116 to A122 of FGF17 (SEQ ID NO:2); and β12 comprises an amino acid sequence exhibiting at least 90% homology to a fragment having residues from about H151 to R155 of FGF17 (SEQ ID NO:2); or ii) β1 comprises an amino acid sequence exhibiting at least 90% homology to a fragment having residues from about Q29 to Y36 of FGF17 (SEQ ID NO: 2); and β4 comprises an amino acid sequence exhibiting at least 90% homology to a fragment having residues from about Q58 to T63 of FGF18 (SEQ ID NO:1); and β9 comprises an amino acid sequence exhibiting at least 90% homology to a fragment having residues from about Y116 to A122 of FGF17 (SEQ ID NO:2); and β12 comprises an amino acid sequence exhibiting at least 90% homology to a fragment having residues from about H151 to R155 of FGF17 (SEQ ID NO:2); or iii) β1 comprises an amino acid sequence exhibiting at least 90% homology to a fragment having residues from about Q29 to Y36 of FGF17 (SEQ ID NO: 2); and β4 comprises an amino acid sequence exhibiting at least 90% homology to a fragment having residues from about K63 to T68 of FGF17 (SEQ ID NO:2); and β9 comprises an amino acid sequence exhibiting at least 90% homology to a fragment having residues from about Y111 to A117 of FGF18 (SEQ ID NO:1); and β12 comprises an amino acid sequence exhibiting at least 90% homology to a fragment having residues from about H151 to R155 of FGF17 (SEQ ID NO:2); or iv) β1 comprises an amino acid sequence exhibiting at least 90% homology to a fragment having residues from about Q29 to Y36 of FGF17 (SEQ ID NO: 2); and β4 comprises an amino acid sequence exhibiting at least 90% homology to a fragment having residues from about K63 to T68 of FGF17 (SEQ ID NO:2); and β9 comprises an amino acid sequence exhibiting at least 90% homology to a fragment having residues from about Y116 to A122 of FGF17 (SEQ ID NO:2); β12 comprises an amino acid sequence exhibiting at least 90% homology to a fragment having residues from about H146 to R150 of FGF18 (SEQ ID NO:1); or v) β1 comprises an amino acid sequence exhibiting at least 90% homology to a fragment having residues from about Q24 to Y31 of FGF18 (SEQ ID NO:1); and β4 comprises an amino acid sequence exhibiting at least 90% homology to a fragment having residues from about Q58 to T63 of FGF18 (SEQ ID NO:1); and β9 comprises an amino acid sequence exhibiting at least 90% homology to a fragment having residues from about Y116 to A122 of FGF17 (SEQ ID NO:2); and β12 comprises an amino acid sequence exhibiting at least 90% homology to a fragment having residues from about H151 to R155 of FGF17 (SEQ ID NO:2); or vi) β1 comprises an amino acid sequence exhibiting at least 90% homology to a fragment having residues from about Q24 to Y31 of FGF18 (SEQ ID NO:1); and β4 comprises an amino acid sequence exhibiting at least 90% homology to a fragment having residues from about K63 to T68 of FGF17 (SEQ ID NO:2); and β9 comprises an amino acid sequence exhibiting at least 90% homology to a fragment having residues from about Y111 to A117 of FGF18 (SEQ ID NO:1); and β12 comprises an amino acid sequence exhibiting at least 90% homology to a fragment having residues from about H151 to R155 of FGF17 (SEQ ID NO:2); or vii) β1 comprises an amino acid sequence exhibiting at least 90% homology to a fragment having residues from about Q24 to Y31 of FGF18 (SEQ ID NO:1); and β4 comprises an amino acid sequence exhibiting at least 90% homology to a fragment having residues from about K63 to T68 of FGF17 (SEQ ID NO:2); and β9 comprises an amino acid sequence exhibiting at least 90% homology to a fragment having residues from about Y116 to A122 of FGF17 (SEQ ID NO:2); and β12 comprises an amino acid sequence exhibiting at least 90% homology to a fragment having residues from about H146 to R150 of FGF18 (SEQ ID NO:1); or viii) β1 comprises an amino acid sequence exhibiting at least 90% homology to a fragment having residues from about Q29 to Y36 of FGF17 (SEQ ID NO: 2); and β4 comprises an amino acid sequence exhibiting at least 90% homology to a fragment having residues from about K63 to T68 of FGF17 (SEQ ID NO:2); and β9 comprises an amino acid sequence exhibiting at least 90% homology to a fragment having residues from about Y111 to A117 of FGF18 (SEQ ID NO:1); and β12 comprises an amino acid sequence exhibiting at least 90% homology to a fragment having residues from about H146 to R150 of FGF18 (SEQ ID NO:1); or ix) β1 comprises an amino acid sequence exhibiting at least 90% homology to a fragment having residues from about Q29 to Y36 of FGF17 (SEQ ID NO: 2); and β4 comprises an amino acid sequence exhibiting at least 90% homology to a fragment having residues from about Q58 to T63 of FGF18 (SEQ ID NO:1); and β9 comprises an amino acid sequence exhibiting at least 90% homology to a fragment having residues from about Y116 to A122 of FGF17 (SEQ ID NO:2); β12 comprises an amino acid sequence exhibiting at least 90% homology to a fragment having residues from about H146 to R150 of FGF18 (SEQ ID NO:1); or x) β1 comprises an amino acid sequence exhibiting at least 90% homology to a fragment having residues from about Q29 to Y36 of FGF17 (SEQ ID NO: 2); and β4 comprises an amino acid sequence exhibiting at least 90% homology to a fragment having residues from about Q58 to T63 of FGF18 (SEQ ID NO:1); and β9 comprises an amino acid sequence exhibiting at least 90% homology to a fragment having residues from about Y111 to A117 of FGF18 (SEQ ID NO:1); and β12 comprises an amino acid sequence exhibiting at least 90% homology to a fragment having residues from about H151 to R155 of FGF17 (SEQ ID NO:2); or xi) β1 comprises an amino acid sequence exhibiting at least 90% homology to a fragment having residues from about Q24 to Y31 of FGF18 (SEQ ID NO:1); and β4 comprises an amino acid sequence exhibiting at least 90% homology to a fragment having residues from about K63 to T68 of FGF17 (SEQ ID NO:2); and β9 comprises an amino acid sequence exhibiting at least 90% homology to a fragment having residues from about Y111 to A117 of FGF18 (SEQ ID NO:1); and β12 comprises an amino acid sequence exhibiting at least 90% homology to a fragment having residues from about H146 to R150 of FGF18 (SEQ ID NO:1); or xii) β1 comprises an amino acid sequence exhibiting at least 90% homology to a fragment having residues from about Q24 to Y31 of FGF18 (SEQ ID NO:1); and β4 comprises an amino acid sequence exhibiting at least 90% homology to a fragment having residues from about Q58 to T63 of FGF18 (SEQ ID NO:1); and β9 comprises an amino acid sequence exhibiting at least 90% homology to a fragment having residues from about Y116 to A122 of FGF17 (SEQ ID NO:2); β12 comprises an amino acid sequence exhibiting at least 90% homology to a fragment having residues from about H146 to R150 of FGF18 (SEQ ID NO:1); or xiii) β1 comprises an amino acid sequence exhibiting at least 90% homology to a fragment having residues from about Q24 to Y31 of FGF18 (SEQ ID NO:1); and β4 comprises an amino acid sequence exhibiting at least 90% homology to a fragment having residues from about Q58 to T63 of FGF18 (SEQ ID NO:1); and β9 comprises an amino acid sequence exhibiting at least 90% homology to a fragment having residues from about Y111 to A117 of FGF18 (SEQ ID NO:1); and β12 comprises an amino acid sequence exhibiting at least 90% homology to a fragment having residues from about H151 to R155 of FGF17 (SEQ ID NO:2); or xiv) β1 comprises an amino acid sequence exhibiting at least 90% homology to a fragment having residues from about Q29 to Y36 of FGF17 (SEQ ID NO: 2); and β4 comprises an amino acid sequence exhibiting at least 90% homology to a fragment having residues from about Q58 to T63 of FGF18 (SEQ ID NO:1); and β9 comprises an amino acid sequence exhibiting at least 90% homology to a fragment having residues from about Y111 to A117 of FGF18 (SEQ ID NO:1); and β12 comprises an amino acid sequence exhibiting at least 90% homology to a fragment having residues from about H146 to R150 of FGF18 (SEQ ID NO:1).

In some embodiments, β1 is identical to a fragment having residues from about Q24 to Y31 of FGF18 (SEQ ID NO: 1).

In some embodiments, β1 is identical to a fragment having residues from about Q29 to Y36 of FGF17 (SEQ ID NO: 2).

In some embodiments, β4 is identical to a fragment having residues from about Q58 to T63 of FGF18 (SEQ ID NO: 1).

In some embodiments, β4 is identical to a fragment having residues from about T68 of FGF17 (SEQ ID NO: 2).

In some embodiments, β9 is identical to a fragment having residues from about Y111 to A117 of FGF18 (SEQ ID NO: 1).

In some embodiments, β9 is identical to a fragment having residues from about Y116 to A122 of FGF17 (SEQ ID NO: 2).

In some embodiments, β12 is identical to a fragment having residues from about H146 to R150 of FGF18 (SEQ ID NO: 1).

In some embodiments, β12 is identical to a fragment having residues from about H151 to R155 of FGF17 (SEQ ID NO: 2).

In some embodiments, the fusion polypeptide further comprises at least one modification in an amino acid residue corresponding to that in FGF18 (SEQ ID NO: 1), wherein said at least one modification is selected from the group consisting of Y151L, P152Y, K153Q, 156aL, 156bP, 156cF, 156dP, 156eN, 156fH, P156A, L158K, P161Q, K163E, Y164F, 165aV, 165bG, 165cS, 165dA, 165eP, T166R, V167R, S171T, I174P, R175Q, T177L, H178T, des P179, and des A180.

In some embodiments, the fusion polypeptide further comprises at least one modification in an amino acid residue corresponding to that in FGF17 (SEQ ID NO: 2), wherein said at least one modification is selected from the group consisting of I30L, E32L, L156Y, Y157P, Q158K, des L161, des P162, des F163, des P164, des N165, des H166, A167P, K169L, Q172P, E174K, F175Y, des V176, des G177, des S178, des A179, des P180, R182T, R183V, T187S, P190I, Q191R, L193T, T194H, 195aP, and 195bA.

In some embodiments, the fusion polypeptide further comprises a fusion site comprising a sequence of at least about 6 amino acids that is identical to a corresponding sequence in FGF18 (SEQ ID NO: 1) and FGF17 (SEQ ID NO: 2). In some embodiments, the fusion site comprises a sequence of at least about 8 amino acids that is identical to a corresponding sequence in FGF18 (SEQ ID NO: 1) and FGF17 (SEQ ID NO: 2). In some embodiments, the fusion site comprises a sequence of about 6-25 amino acids that is identical to a corresponding sequence in FGF18 (SEQ ID NO: 1) and FGF17 (SEQ ID NO: 2).

In some embodiments, the fusion polypeptide retains the secondary structure of FGF18 (SEQ ID NO: 1) or FGF17 (SEQ ID NO: 2).

In some embodiments, the fusion polypeptide is devoid of any additional T-epitope as compared to that of FGF18 (SEQ ID NO: 1) or FGF17 (SEQ ID NO: 2).

In some embodiments, the fusion polypeptide is devoid of any additional B-epitope as compared to that of FGF18 (SEQ ID NO: 1) or FGF17 (SEQ ID NO: 2).

In some embodiments, the fusion polypeptide exhibits less than about 90% sequence homology to FGF18 (SEQ ID NO: 1) or FGF17 (SEQ ID NO: 2).

In some embodiments, the fusion polypeptide exhibits less than about 95% sequence homology to FGF18 (SEQ ID NO: 1) or FGF17 (SEQ ID NO: 2).

In some embodiments, the N-terminus of the fusion polypeptide is further modified by a polyethylene glycol (PEG). In some embodiments, the polyethylene glycol is monomethoxy PEG propionaldehyde. In some embodiments, the polyethylene glycol has a molecular weight of about 12 Kd to 40 Kd.

In some embodiments, the fusion polypeptide exhibits a prolonged in vivo half-life as compared to FGF18 (SEQ ID NO: 1) or FGF17 (SEQ ID NO: 2).

In some embodiments, the fusion polypeptide exhibits an enhanced chemistry stability as compared to FGF18 (SEQ ID NO: 1) or FGF17 (SEQ ID NO: 2).

In some embodiments, the fusion polypeptide comprises an amino acid sequence selected from the group consisting of SEQ ID NO:3, SEQ ID NO:4, SEQ ID NO:5, SEQ ID NO: 6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

In another aspect, the present disclosure provides a host cell expressing the fusion polypeptide of the present disclosure. In some embodiments, the host cell is a prokaryotic cell.

In a further aspect, the present disclosure provides a method of treating a cartilage defect in a mammal in need thereof, comprising administering to the mammal a therapeutically effective amount of the fusion polypeptide or its pegylated derivative as described in the present disclosure. In some embodiments, the cartilage defect is selected from the group consisting of osteoarthritis, degenerative disc disease, and cartilage injury. In some embodiments, said treating a cartilage defect is cartilage repair, e.g., cartilage microfracture surgery.

In another aspect, the present disclosure provides use of the fusion polypeptide or its pegylated derivative as described in the present disclosure in the preparation of a composition for treating a cartilage defect in a mammal in need thereof. In some embodiments, the cartilage defect is selected from the group consisting of osteoarthritis, degenerative disc disease, and cartilage injury. In some embodiments, said treating a cartilage defect is cartilage repair, e.g., cartilage microfracture surgery. In some embodiments, the composition is a pharmaceutical composition. In some embodiments, the composition is formulated into a medicament.

In yet another aspect, the present disclosure provides a pharmaceutical composition comprising at least one of the fusion polypeptides or its pegylated derivative of the present disclosure, and a pharmaceutically acceptable excipient.

In some embodiments, the present disclosure provides a pharmaceutical composition comprising at least one of the fusion polypeptides or its pegylated derivative of the present disclosure and a second therapeutic agent.

In another aspect, the present disclosure provides a vector comprising a polynucleotide encoding the fusion polypeptide of the present disclosure. In a further aspect, the present disclosure provides a method of producing the fusion polypeptide of the present disclosure, comprising expressing the vector in a cell under conditions suitable for protein expression, thereby producing the fusion polypeptide.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
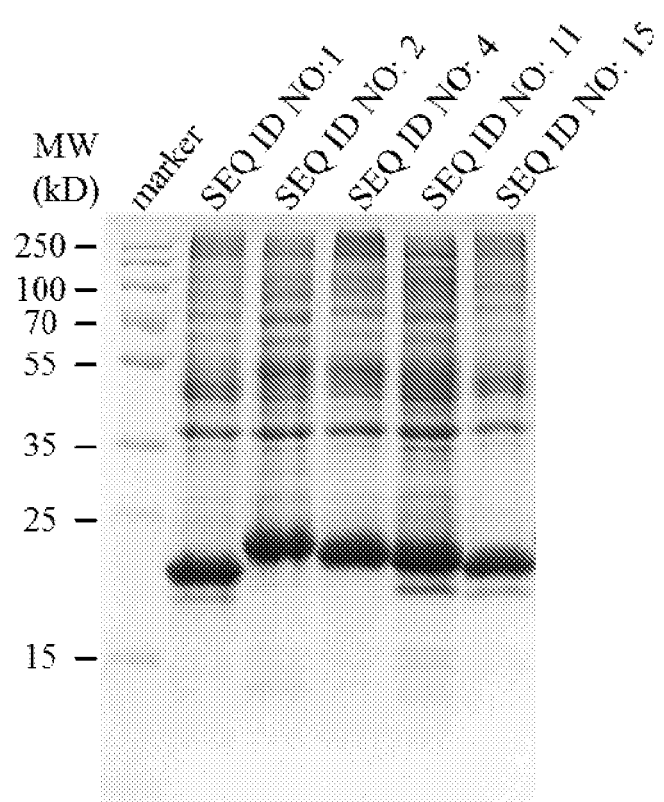
FIG. 1 illustrates the SDS-PAGE analysis of solubilized inclusion bodies following the protein expression of fusion polypeptides and their reference polypeptides (SEQ ID NO: 1, 2, 4, 11, and 15) using the methods of the present disclosure.

Before the embodiments of the disclosure are described, it is to be understood that such embodiments are provided by way of example only, and that various alternatives to the embodiments of the disclosure described herein may be employed in practicing the disclosure. Numerous variations, changes, and substitutions will now occur to those skilled in the art without departing from the disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the disclosure.

As used in the specification and claims, the singular form "a", "an" and "the" include plural references unless the context clearly dictates otherwise.

The terms "polypeptide", "peptide", and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component.

The term "amino acid" refers to either natural and/or unnatural or synthetic amino acids, including but not limited to both the D or L optical isomers, and amino acid analogs and peptidomimetics. Standard single or three letter codes are used to designate amino acids.

The term "natural L-amino acid" means the L optical isomer forms of glycine (G), proline (P), alanine (A), valine (V), leucine (L), isoleucine (I), methionine (M), cysteine (C), phenylalanine (F), tyrosine (Y), tryptophan (W), histidine (H), lysine (K), arginine (R), glutamine (Q), asparagine (N), glutamic acid (E), aspartic acid (D), serine (S), and threonine (T).

The term "non-naturally occurring," as applied to sequences and as used herein, means polypeptide or polynucleotide sequences that do not have a counterpart to, are not complementary to, or do not have a high degree of homology with a wild-type or naturally-occurring sequence found in a mammal. For example, a non-naturally occurring polypeptide or fragment may share less than 99%, 98%, 95%, 90%, 80%, 70%, 60%, 50% or even less amino acid sequence identity as compared to a natural sequence when suitably aligned. Alternatively, a non-naturally occurring polypeptide or fragment may share more than 99%, 98%, 95%, 90%, 80%, 70%, 60%, 50% or even more amino acid sequence identity as compared to a natural sequence when suitably aligned.

The terms "hydrophilic" and "hydrophobic" refer to the degree of affinity that a substance has with water. A hydrophilic substance has a strong affinity for water, tending to dissolve in, mix with, or be wetted by water, while a hydrophobic substance substantially lacks affinity for water, tending to repel and not absorb water and tending not to dissolve in or mix with or be wetted by water. Amino acids can be characterized based on their hydrophobicity. A number of scales have been developed. An example is a scale developed by Levitt, M, et al., J Mol Biol (1976) 104:59, which is listed in Hopp, T P, et al., Proc Natl Acad Sci USA (1981) 78:3824. Examples of "hydrophilic amino acids" are arginine, lysine, threonine, alanine, asparagine, and glutamine. Of particular interest are the hydrophilic amino acids aspartate, glutamate, and serine, and glycine. Examples of "hydrophobic amino acids" are tryptophan, tyrosine, phenylalanine, methionine, leucine, isoleucine, and valine.

A "fragment" when applied to a protein, is a truncated form of a native biologically active protein that may or may not retain a portion of the therapeutic and/or biological activity. A "variant" when applied to a protein is a protein with sequence homology to the native biologically active protein that retains at least a portion of the therapeutic and/or biological activity of the biologically active protein. For example, a variant protein may share at least 70%, 75%, 80%, 85%, 90%, 95%, 96%, 97%, 98% or 99% amino acid sequence identity compared with the reference biologically active protein. As used herein, the term "biologically active protein moiety" includes proteins modified deliberately, as for example, by site directed mutagenesis, synthesis of the encoding gene, insertions, or accidentally through mutations.

"Conjugated", "linked," "fused," and "fusion" are used interchangeably herein. These terms refer to the joining together of two or more chemical elements, sequences or components, by whatever means including chemical conjugation or recombinant means. For example, a promoter or enhancer is operably linked to a coding sequence if it affects the transcription of the sequence. Generally, "operably linked" means that the DNA sequences being linked are contiguous, and in reading phase or in-frame. An "in-frame fusion" refers to the joining of two or more open reading frames (ORFs) to form a continuous longer ORF, in a manner that maintains the correct reading frame of the original ORFs. Thus, the resulting "fusion polypeptide" is a single protein containing two or more fragments that correspond to polypeptides encoded by the original ORFs (which segments are not normally so joined in nature). The "fusion site" refers to the sequence where the two or more fragments are joined together. In some cases, the fusion site can be a sequence that is identical to sequences in the two or more fragments being joined. For example, the fusion site can comprise a sequence of about 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acids that are identical to sequences in the fragments being joined. In some embodiments, the fusion site can comprise a sequence of about 6, 7, 8, 9, 10, 11, 12, 13, 14, 15, 16, 17, 18, 19, 20, 21, 22, 23, 24, 25, 26, 27, 28, 29, 30 or more amino acids that are identical to sequences in the fragments being joined. For example, the fusion site can comprise a sequence of about 6, 7, 8, 9, 10, 11, 12, 13, 14, 15, 16, 17, 18 amino acids that are identical to sequences in the fragments being joined. In some cases, the fusion site can further comprise a gap segment that is not identical to either of the sequences of the two or more fragments being joined. The gap segment may be found within the amino acid sequence of the fusion site. Further, the gap segment may comprise 1, 2, 3, 4, 5, 6, 7, 8, 9, or 10 amino acids. For example, the fusion site can comprise 8 amino acids that are each identical to one or both of the two fragments, and a gap segment of 2 amino acids within the 8 amino acid sequence that is not identical to either of the sequences of the two or more fragments being joined.

In the context of polypeptides, a "linear sequence" or a "sequence" is an order of amino acids in a polypeptide in an amino to carboxyl terminus direction in which residues next to each other in the sequence are contiguous in the primary structure of the polypeptide. A "partial sequence" is a linear sequence forming part of a polypeptide that is known to comprise additional residues in one or both directions.

In the present disclosure, the terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "gene" and "gene fragment" are used interchangeably herein. They refer to a polynucleotide containing at least one open reading frame that is capable of encoding a particular protein after being transcribed and translated. A gene or gene fragment may be genomic or cDNA, as long as the polynucleotide contains at least one open reading frame, which may cover the entire coding region or a segment thereof. A "fusion gene" is a gene composed of at least two heterologous polynucleotides that are linked together.

"Homology" or "homologous" or "sequence identity" refers to sequence similarity or interchangeability between two or more polynucleotide sequences or between two or more polypeptide sequences. When using a program (e.g. Emboss Needle or BestFit) to determine sequence identity, similarity or homology between two different amino acid sequences, the default settings may be used, or an appropriate scoring matrix, such as blosum45 or blosum80, may be selected to optimize identity, similarity or homology scores. Preferably, polynucleotides that are homologous are those which hybridize under stringent conditions as defined herein and have at least 70%, preferably at least 80%, more preferably at least 90%, more preferably 95%, more preferably 97%, more preferably 98%, and even more preferably 99% sequence identity compared to those sequences. Polypeptides that are homologous preferably have sequence identities of at least 80%, or at least 90%, or at least 95%, or at least 97%, or at least 98%, or have at least 99% sequence identity when sequences of comparable length are optimally aligned.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity may be measured over the length of an entire defined polynucleotide sequence, or may be measured over a shorter length, for example, over the length of a fragment taken from a larger, defined polynucleotide sequence, for instance, a fragment of at least 45, at least 60, at least 90, at least 120, at least 150, at least 210 or at least 450 contiguous residues. Such lengths are exemplary only, and it is understood that any fragment length supported by the sequences shown herein, in the tables, figures or Sequence Listing, may be used to describe a length over which percentage identity may be measured.

"Percent (%) sequence identity," with respect to the polypeptide sequences identified herein, is defined as the percentage of amino acid residues in a query sequence that are identical with the amino acid residues of a second, reference polypeptide sequence or a portion thereof, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, NEEDLE or Megalign (DNASTAR) software. Those skilled in the art can determine appropriate parameters for measuring alignment, including any algorithms needed to achieve maximal alignment over the full length of the sequences being compared. Percent identity may be measured over the length of an entire defined polypeptide sequence, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vitro with a vector of the present disclosure. In some cases, a host cell is a prokaryotic cell. In some examples, the prokaryotic cell is *E. coli*.

A "vector" is a nucleic acid molecule, preferably self-replicating in an appropriate host, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. target gene induction, proliferation, and/or apoptosis. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

"therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal so that both agents and/or their metabolites are present in the subject at the same time. Co-administration includes simultaneous administration in separate compositions, administration at different times in separate compositions, or administration in a composition in which both agents are present.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like, when the molecule contains an acidic functionality; and when the molecule contains a basic functionality, salts of organic or inorganic acids, such as hydrochloride, hydrobromide, tartrate, mesylate (methane sulfonate), ethane sulfonate, acetate, maleate, oxalate, phosphate, and the like. In a compound with more than one basic moiety, more than one of the basic moieties may be converted to the salt form, including but not limited to a bis- or tris-salt. Alternatively, a compound having more than one basic moiety may form a salt at only one of the basic moieties.

The terms "antagonist" and "inhibitor" are used interchangeably herein, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting or enhancing the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. For example, cell proliferation may result in an increase in number of cells. This term also encompasses cell growth by which the cell morphology has changed (e.g., increased in size) consistent with a proliferative signal.

The term "selective inhibition" or "selectively inhibit" refers to a biologically active agent's ability to preferentially reduce the target signaling activity as compared to off-target signaling activity, via direct or indirect interaction with the target.

The term "in vivo" refers to an event that takes place in a subject's body.

The term "in vitro" refers to an event that takes places outside of a subject's body. For example, an in vitro assay encompasses any assay conducted outside of a subject. In vitro assays encompass cell-based assays in which dead or living cells are employed. In vitro assays also encompass a cell-free assay in which no intact cells are employed.

Nomenclature of Polypeptides

Polypeptides are named herein using, interchangeably, polypeptide nomenclature, organic chemical nomenclature, chemical formula, amino acid sequences, or a mix thereof. For example, a substitution in an analogue of FGF18 maybe indicated as "Original amino acid-position-substituted amino acid".

Accordingly, the notation "L25IFGF18" or "Leu25Ile FGF18" means that the FGF18 analogue comprises a substitution of leucine with isoleucine at the analogue amino acid position corresponding to the amino acid at position 25 in FGF18 (SEQ ID NO: 1) when the analogue and FGF18 are aligned as described below ("alignment"). Multiple substitutions may be separated by commas (with a space after the comma) and surrounded by brackets in order to make it clear that they belong to the same analogue. Accordingly, "(L251, L27E) FGF18" means that the FGF18 analogue comprises two substitutions (leucine with isoleucine and leucine with glutamic acid, respectively) at the analogue amino acid positions corresponding to the amino acid at positions 25 and 27 in FGF18 (SEQ ID NO:1) respectively.

An extension in an analogue of FGF18 may be described by reference to SEQ ID NO: 1 by addition of position numbers (continued positive numbers in the C-terminus and negative numbers in the N-terminus) or, more simply, by adding the amino acids of the extension in question, using the correct sequence thereof, to the compound in question. Accordingly, M-FGF18 designates the polypeptide of SEQ ID NO: 1 with an M at position −1 by reference to SEQ ID NO: 1.

An insertion in an analogue of FGF18 may be described as: "Amino acid position number before the insertion-index-inserted amino acid". The amino acid position number before the insertion refers to the amino acid position in FGF18 (SEQ ID NO: 1) just before the gap, which is created when the insertion analogue and FGF18 are aligned as described below ("alignment"). The index is a lower case letter in alphabetical order, e.g. "a" for the first inserted amino acid, "b" for the second inserted amino acid, etc. Accordingly, "82aG FGF18" designates an analogue of FGF18 with an insertion of glycine after amino acid position 82 in FGF18 (SEQ ID NO: 1).

A deletion in an analogue of FGF18 may be described as: "des Deleted amino acid-deleted amino acid position" or "d Deleted amino acid-deleted amino acid position". The deleted amino acid position refers to the amino acid position in FGF18 (SEQ ID NO: 1) at the gap, which is created when the analogue and FGF18 are aligned as described below ("alignment"). Accordingly, "des L25 FGF18" designates an analogue of FGF18 with a deletion of the leucine residue at position 25 in FGF18 (SEQ ID NO: 1).

Where desired, the alignment of two amino acid sequences may be made by using the Needle program from the EMBOSS package (http://www.ebi.ac.uk/Tools/psa/emboss needle/). The Needle program implements a global alignment algorithm (J. Mol. Biol. 1970, 48:443-453). The substitution matrix used is BLOSUM62, gap opening penalty is 50, and gap extension penalty is 0.5.

Fusion Polypeptides, Host Cells and Vectors

The present disclosure relates to fusion polypeptides that are useful for the treatment of disease conditions in mammals. The fusion polypeptide can comprise a first fragment from a first member and a second fragment from a second member of a protein family. In some cases, the first and second members can both be members of the same protein family. In other cases, the first and second member can belong to different protein families. In certain embodiments, the first and/or the second member belong to FGF family. In some examples, the fusion polypeptides can comprise fragments from a first and a second FGF family member (or isoforms thereof). Examples of FGF family members include but are not limited FGF18, FGF17 and FGF8, and various isoforms thereof. In some examples, the first FGF family member is FGF18 or an isoform thereof, including but not limited to those as set forth in SEQ ID NO: 1. In some examples, the second FGF family member is FGF17 or an isoform thereof, including but not limited to those as set forth in SEQ ID NO: 2. In further examples, the first FGF family member is FGF18 or an isoform thereof and the second FGF family member is FGF17 or an isoform thereof.

In some cases, the fragments can be fused together at a fusion site and thereby forming a contiguous polypeptide. In some examples, the fusion site can comprise a sequence of at least about 6 amino acids that are identical to a corresponding sequence found in the first and the second family member. In further examples, the fusion site can comprise a sequence of about 8, 9, 10, 11, 12, 13, 14, 15, 16, 17, 18, 19, 20, 21, 22, 23, 24, 25, 26, 27, 28, 29, 30 or more amino acids that are identical to a corresponding sequence found in the first and the second members. In the cases wherein each of the first and the second member is an FGF family member, the fusion site can comprise a sequence of about 8, 9, 10, or 11 amino acids that are identical to a corresponding sequence found in the first and the second FGF family members, isoforms and/or mutants thereof.

In some cases, the fusion polypeptide can have a structure of Formula I:

(S1)-(β1)-(S2)-(β2)-(S3)-(β3)-(S4)-(β4)-(S5)-(β5)-(S6)-(β6)-(S7)-(β7)-(S8)-(β8)-(S9)-(β9)-(S10)-(β10)-(S11)-(β11)-(S12)-(β12)-S13 wherein each of β1, β2, β3, β4, β5, β6, β7, β8, β9, β10, β11, and β12 is independently a β-sheet, and wherein each of S1, S2, S3, S4, S5, S6, S7, S8, S9, S10, S11, S12, and S13 is independently a spacer sequence.

In some cases, β1 can comprise an amino acid sequence exhibiting at least about 50%, 60%, 70%, 80%, 90%, 95%, 99% or 100% homology to a fragment having residues from about Q24 to Y31 of FGF18 (SEQ ID NO:1) or from about Q29 to Y36 of FGF17 (SEQ ID NO:2). In some examples, β1 can be identical to a fragment having residues from about Q24 to Y31 of FGF18 (SEQ ID NO:1). In other examples, β1 can be identical to a fragment having residues from about Q29 to Y36 of FGF17 (SEQ ID NO: 2).

In some cases, β4 can comprise an amino acid sequence exhibiting at least about 50%, 60%, 70%, 80%, 90%, 95%, 99% or 100% homology to a fragment having residues from about Q58 to T63 of FGF18 (SEQ ID NO:1) or from about K63 to T68 of FGF17 (SEQ ID NO:2). In some examples, β4 can be identical to a fragment having residues from about Q58 to T63 of FGF18 (SEQ ID NO:1). In other examples, β4 can be identical to a fragment having residues from about K63 to T68 of FGF17 (SEQ ID NO:2).

In some cases, β9 can comprise an amino acid sequence exhibiting at least about 50%, 60%, 70%, 80%, 90%, 95%, 99% or 100% homology to a fragment having residues from about Y111 to A117 of FGF18 (SEQ ID NO:1) or from about Y116 to A122 of FGF17 (SEQ ID NO:2). In some examples, β9 can be identical to a fragment having residues from about Y111 to A117 of FGF18 (SEQ ID NO:1). In other examples, β9 can be identical to a fragment having residues from about Y116 to A122 of FGF17 (SEQ ID NO:2).

In some cases, β12 can comprise an amino acid sequence exhibiting at least about 50%, 60%, 70%, 80%, 90%, 95%, 99% or 100% homology to a fragment having residues from about H146 to R150 of FGF18 (SEQ ID NO:1) or from about H151 to R155 of FGF17 (SEQ ID NO:2). In some examples, β12 can be identical to a fragment having residues from about H146 to R150 of FGF18 (SEQ ID NO:1). In other examples, β12 can be identical to a fragment having residues from about H151 to R155 of FGF17 (SEQ ID NO:2).

In some cases, each of S1, S2, S3, S4, S5, S6, S7, S8, S9, S10, S11, S12 and S13 can independently have between 1 to about 5, between 1 to about 10, between 1 to about 15, between 1 to about 20, between 1 to about 30, between 1 to about 40, between 1 to about 50, between 1 to about 60, between 1 to about 70, between 1 to about 80, between 1 to about 90, or between 1 to about 100 amino acid residues.

In some embodiments, β1 can comprise an amino acid sequence exhibiting at least about 80%, 90%, 95%, 99% or 100% homology to a fragment having residues from about Q24 to Y31 of FGF18 (SEQ ID NO:1), β4 can comprise an amino acid sequence exhibiting at least about 80%, 90%, 95%, 99% or 100% homology to a fragment having residues from about K63 to T68 of FGF17 (SEQ ID NO:2), β9 can comprise an amino acid sequence exhibiting at least about 80%, 90%, 95%, 99% or 100% homology to a fragment having residues from about Y116 to A122 of FGF17 (SEQ ID NO:2), and β12 can comprise an amino acid sequence exhibiting at least about 80%, 90%, 95%, 99% or 100% homology to a fragment having residues from about H151 to R155 of FGF17 (SEQ ID NO:2). For example, β1 can comprise an amino acid sequence exhibiting at least 95% homology to a fragment having residues from about Q24 to Y31 of FGF18 (SEQ ID NO:1), β4 can comprise an amino acid sequence exhibiting at least 95% homology to a fragment having residues from about K63 to T68 of FGF17 (SEQ ID NO:2), β9 can comprise an amino acid sequence exhibiting at least 95% homology to a fragment having residues from about Y116 to A122 of FGF17 (SEQ ID NO:2), and β12 can comprise an amino acid sequence exhibiting at least 95% homology to a fragment having residues from about H151 to R155 of FGF17 (SEQ ID NO:2).

In other embodiments, β1 can comprise an amino acid sequence exhibiting at least about 80%, 90%, 95%, 99% or 100% homology to a fragment having residues from about Q29 to Y36 of FGF17 (SEQ ID NO:2), β4 can comprise an amino acid sequence exhibiting at least about 80%, 90%, 95%, 99% or 100% homology to a fragment having residues from about Q58 to T63 of FGF18 (SEQ ID NO:1), β9 can comprise an amino acid sequence exhibiting at least about 80%, 90%, 95%, 99% or 100% homology to a fragment having residues from about Y111 to A117 of FGF18 (SEQ ID NO:1), and β12 can comprise an amino acid sequence exhibiting at least about 80%, 90%, 95%, 99% or 100% homology to a fragment having residues from about H146 to R150 of FGF18 (SEQ ID NO:1). For example, β1 can comprise an amino acid sequence exhibiting at least 95% homology to a fragment having residues from about Q29 to Y36 of FGF17 (SEQ ID NO:2), β4 can comprise an amino acid sequence exhibiting at least 95% homology to a fragment having residues from about Q58 to T63 of FGF18 (SEQ ID NO:1), β9 can comprise an amino acid sequence exhibiting at least 95% homology to a fragment having residues from about Y111 to A117 of FGF18 (SEQ ID NO:1), and β12 can comprise an amino acid sequence exhibiting at least 95% homology to a fragment having residues from about H146 to R150 of FGF18 (SEQ ID NO:1).

In yet other embodiments, β1 can comprise an amino acid sequence exhibiting at least about 80%, 90%, 95%, 99% or 100% homology to a fragment having residues from about Q24 to Y31 of FGF18 (SEQ ID NO:1), β4 can comprise an amino acid sequence exhibiting at least about 80%, 90%, 95%, 99% or 100% homology to a fragment having residues from about Q58 to T63 of FGF18 (SEQ ID NO:1), β9 can comprise an amino acid sequence exhibiting at least about 80%, 90%, 95%, 99% or 100% homology to a fragment having residues from about Y116 to A122 of FGF17 (SEQ ID NO:2), and β12 can comprise an amino acid sequence exhibiting at least about 80%, 90%, 95%, 99% or 100% homology to a fragment having residues from about H151 to R155 of FGF17 (SEQ ID NO:2). For example, β1 can comprise an amino acid sequence exhibiting at least 95% homology to a fragment having residues from about Q24 to Y31 of FGF18 (SEQ ID NO:1), β4 can comprise an amino acid sequence exhibiting at least 95% homology to a fragment having residues from about Q58 to T63 of FGF18 (SEQ ID NO:1), β9 can comprise an amino acid sequence exhibiting at least 95% homology to a fragment having residues from about Y116 to A122 of FGF17 (SEQ ID NO:2), and β12 can comprise an amino acid sequence exhibiting at least 95% homology to a fragment having residues from about H151 to R155 of FGF17 (SEQ ID NO:2).

In other embodiments, β1 can comprise an amino acid sequence exhibiting at least about 80%, 90%, 95%, 99% or 100% homology to a fragment having residues from about Q29 to Y36 of FGF17 (SEQ ID NO:2), β4 can comprise an amino acid sequence exhibiting at least about 80%, 90%, 95%, 99% or 100% homology to a fragment having residues from about K63 to T68 of FGF17 (SEQ ID NO:2), β9 can comprise an amino acid sequence exhibiting at least about 80%, 90%, 95%, 99% or 100% homology to a fragment having residues from about Y111 to A117 of FGF18 (SEQ ID NO:1), and β12 can comprise an amino acid sequence exhibiting at least about 80%, 90%, 95%, 99% or 100% homology to a fragment having residues from about H146 to R150 of FGF18 (SEQ ID NO:1). For example, β1 can comprise an amino acid sequence exhibiting at least 95% homology to a fragment having residues from about Q29 to Y36 of FGF17 (SEQ ID NO:2), β4 can comprise an amino acid sequence exhibiting at least 95% homology to a fragment having residues from about K63 to T68 of FGF17 (SEQ ID NO:2), β9 can comprise an amino acid sequence exhibiting at least 95% homology to a fragment having residues from about Y111 to A117 of FGF18 (SEQ ID NO:1), and β12 can comprise an amino acid sequence exhibiting at least 95% homology to a fragment having residues from about H146 to R150 of FGF18 (SEQ ID NO:1).

In yet other embodiments, β1 can comprise an amino acid sequence exhibiting at least about 80%, 90%, 95%, 99% or 100% homology to a fragment having residues from about Q24 to Y31 of FGF18 (SEQ ID NO:1), β4 can comprise an amino acid sequence exhibiting at least about 80%, 90%, 95%, 99% or 100% homology to a fragment having residues from about Q58 to T63 of FGF18 (SEQ ID NO:1), β9 can comprise an amino acid sequence exhibiting at least about 80%, 90%, 95%, 99% or 100% homology to a fragment having residues from about Y111 to A117 of FGF18 (SEQ ID NO:1), and β12 can comprise an amino acid sequence exhibiting at least about 80%, 90%, 95%, 99% or 100% homology to a fragment having residues from about H151 to R155 of FGF17 (SEQ ID NO:2). For example, β1 can comprise an amino acid sequence exhibiting at least 95% homology to a fragment having residues from about Q24 to Y31 of FGF18 (SEQ ID NO:1), β4 can comprise an amino acid sequence exhibiting at least 95% homology to a fragment having residues from about Q58 to T63 of FGF18 (SEQ ID NO:1), β9 can comprise an amino acid sequence exhibiting at least 95% homology to a fragment having residues from about Y111 to A117 of FGF18 (SEQ ID NO:1), and β12 can comprise an amino acid sequence exhibiting at least 95% homology to a fragment having residues from about H151 to R155 of FGF17 (SEQ ID NO:2).

In other embodiments, β1 can comprise an amino acid sequence exhibiting at least about 80%, 90%, 95%, 99% or 100% homology to a fragment having residues from about Q29 to Y36 of FGF17 (SEQ ID NO:2), β4 can comprise an amino acid sequence exhibiting at least about 80%, 90%, 95%, 99% or 100% homology to a fragment having residues from about K63 to T68 of FGF17 (SEQ ID NO:2), β9 can comprise an amino acid sequence exhibiting at least about 80%, 90%, 95%, 99% or 100% homology to a fragment having residues from about Y116 to A122 of FGF17 (SEQ ID NO:2), and β12 can comprise an amino acid sequence exhibiting at least about 80%, 90%, 95%, 99% or 100% homology to a fragment having residues from about H146 to R150 of FGF18 (SEQ ID NO:1). For example, β1 can comprise an amino acid sequence exhibiting at least 95% homology to a fragment having residues from about Q29 to Y36 of FGF17 (SEQ ID NO:2), β4 can comprise an amino acid sequence exhibiting at least 95% homology to a fragment having residues from about K63 to T68 of FGF17 (SEQ ID NO:2), β9 can comprise an amino acid sequence exhibiting at least 95% homology to a fragment having residues from about Y116 to A122 of FGF17 (SEQ ID NO:2), and β12 can comprise an amino acid sequence exhibiting at least 95% homology to a fragment having residues from about H146 to R150 of FGF18 (SEQ ID NO:1).

In some cases, the fusion polypeptides can retain the secondary structure of the first and/or the second member. The secondary structure of a member can be defined by the number and/or order of secondary units including but not limited to alpha-helices and beta-sheets. In some examples, the fusion polypeptide can comprise the same number and order of secondary units as those of the first and/or the second member. In the cases wherein the first and second member are each FGF family members, the fusion polypeptide can retain the secondary structure of FGF18 (SEQ ID NO: 1) or FGF17 (SEQ ID NO: 2).

In some cases, the fusion polypeptides can be substantially free of epitopes recognized by human T cells. The elimination of such epitopes for the purpose of generating less immunogenic proteins has been disclosed previously; see for example WO 98/52976, WO 02/079232, and WO 00/3317 which are incorporated by reference herein. Assays for human T cell epitopes have been described (Stickler, M., et al. (2003) *J Immunol Methods*, 281: 95-108). Of particular interest are peptide sequences that can be oligomerized without generating T-cell epitopes or non-human sequences. This is achieved by testing direct repeats of these sequences for the presence of T-cell epitopes and for the occurrence of 6 to 15-mer and, in particular, 9-mer sequences that are not human, and then altering the design of the XTEN sequence to eliminate or disrupt the epitope sequence. With a reduction in the numbers of epitopes capable of binding to MHC receptors, there is a concomitant reduction in the potential for T cell activation as well as T cell helper function, reduced B cell activation or upregulation and reduced antibody production. The low degree of predicted T-cell epitopes can be determined by epitope prediction algorithms such as, e.g., TEPITOPE (Sturniolo, T., et al. (1999) Nat Biotechnol, 17: 555-61).

In some cases, the fusion polypeptide can be devoid of any additional T-epitope as compared to that of FGF18 (SEQ ID NO: 1) and/or FGF17 (SEQ ID NO: 2). In further cases, the fusion polypeptide can have less T-epitopes as compared to that of FGF18 (SEQ ID NO: 1) and/or FGF17 (SEQ ID NO: 2).

In some cases, the fusion polypeptide can be devoid of any additional B-epitope as compared to that of FGF18 (SEQ ID NO: 1) and/or FGF17 (SEQ ID NO: 2). In further cases, the fusion polypeptide can have less B-epitopes as compared to that of FGF18 (SEQ ID NO: 1) and/or FGF17 (SEQ ID NO: 1).

In various cases, the fusion polypeptides can further comprise at least one modification in an amino acid residue corresponding to FGF18 (SEQ ID NO: 1), wherein the at least one modification is selected from the group consisting of Y151L, P152Y, K153Q, 156aL, 156bP, 156cF, 156dP, 156eN, 156fH, P156A, L158K, P161Q, K163E, Y164F, 165aV, 165bG, 165cS, 165dA, 165eP, T166R, V167R, S171T, I174P, R175Q, T177L, H178T, des P179, and des A180.

In various cases, the fusion polypeptides can further comprise at least one modification in an amino acid residue corresponding to FGF17 (SEQ ID NO: 2), wherein said at least one modification is selected from the group consisting of L156Y, Y157P, Q158K, des L161, des P162, des F163, des P164, des N165, des H166, A167P, K169L, Q172P, E174K, F175Y, des V176, des G177, des S178, des A179, des P180, R182T, R183V, T187S, P190I, Q191R, L193T, T194H, 195aP, and 195bA.

In some cases, the fusion polypeptides can further comprise a fusion site comprising a sequence of about 2, 3, 4, 5, 6, 7, 8, 9 or 10 amino acids that are identical to a corresponding sequence in FGF18 (SEQ ID NO: 1) and FGF17 (SEQ ID NO: 2). In other cases, the fusion site can comprise a sequence of about 11, 12, 13, 14, 15, 16, 17, 18, 19, 20, 21, 22, 23, 24, 25, 26, 27, 28, 29, 30 or more amino acids that are identical to a corresponding sequence in FGF18 (SEQ ID NO: 1) and FGF17 (SEQ ID NO: 2).

In some cases, the fusion site can comprises a sequence of about 2 to 23, about 3 to 20, about 4 to 15, about 5 to 10, about 6 to 9 amino acids that are identical to a corresponding sequence of at least the FGF18 (SEQ ID NO: 1) and FGF17 (SEQ ID NO: 2) isoforms.

In some cases, the fusion polypeptide can exhibit at least about 80%, 81%, 82%, 83%, 84%, 85%, 86%, 87%, 88%, 89%, 90%, 91%, 92%, 93%, 94%, 95%, 96%, 97%, 98%, or 99% sequence homology to FGF18 (SEQ ID NO: 1). For example, the fusion polypeptide can exhibit at least about 90% sequence homology to FGF18 (SEQ ID NO: 1). Further, the fusion polypeptide can exhibit at least about 95% sequence homology to FGF18 (SEQ ID NO: 1).

In some cases, the fusion polypeptide can exhibit less than about 10%, 20%, 30%, 40%, 50%, 60%, 70%, 80%, 90%, 95% or 99% sequence homology to FGF18 (SEQ ID NO: 1). For example, the fusion polypeptide can exhibit less than about 80% sequence homology to FGF18 (SEQ ID NO: 1). Further, the fusion polypeptide can exhibit less than about 50% sequence homology to FGF18 (SEQ ID NO: 1).

In some cases, the fusion polypeptide can exhibit at least about 80%, 81%, 82%, 83%, 84%, 85%, 86%, 87%, 88%, 89%, 90%, 91%, 92%, 93%, 94%, 95%, 96%, 97%, 98%, or 99% sequence homology to FGF17 (SEQ ID NO: 2). For example, the fusion polypeptide can exhibit at least about 90% sequence homology to FGF17 (SEQ ID NO: 2). Further, the fusion polypeptide can exhibit at least about 95% sequence homology to FGF17 (SEQ ID NO: 2).

In some cases, the fusion polypeptide can exhibit less than about 10%, 20%, 30%, 40%, 50%, 60%, 70%, 80%, 90%, 95% or 99% sequence homology to FGF17 (SEQ ID NO: 2). For example, the fusion polypeptide can exhibit less than about 90% sequence homology to FGF17 (SEQ ID NO: 2).

Further, the fusion polypeptide can exhibit less than about 50% sequence homology to FGF17 (SEQ ID NO: 2).

In some cases, the fusion polypeptide can be further modified. The modification can occur at either the N-terminus, C-terminus, or at any reactive amino acid side chain.

In some embodiments, the fusion polypeptide can be further modified by a polyethylene glycol (PEG). Examples of polyethylene glycol include but are not limited to monomethoxy PEG maleimide, monomethoxy PEG iodoacetamide or monomethoxy PEG propionaldehyde. Further, the polyethylene glycol can have a molecular weight of about 1 Kd to 200 Kd, about 5 Kd to 200 Kd, about 5 Kd to 150 Kd, about 8 Kd to 150 Kd, about 8 Kd to 100 Kd, about 10 Kd to 100 Kd, about 10 Kd to 50 Kd, about 12 Kd to 50 Kd, or about 12 Kd to 40 Kd.

In some cases, the PEGylated fusion polypeptide can exhibit a prolonged in vitro half-life as compared to the first and/or the second member of the protein family. For example, the fusion polypeptide can exhibit a prolonged in vitro half-life as compared to FGF18 (SEQ ID NO: 1) and/or FGF17 (SEQ ID NO:2).

In some cases, the fusion polypeptide can exhibit enhanced chemistry stability as compared to the first and/or the second member of the protein family. For example, the fusion polypeptide can exhibit enhanced chemistry stability as compared to FGF18 (SEQ ID NO: 1) and/or FGF17 (SEQ ID NO: 2).

The fusion polypeptide can comprise an amino acid sequence selected from group consisting of SEQ ID NO:3, SEQ ID NO:4, SEQ ID NO:5, SEQ ID NO: 6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16. In some embodiments, the fusion polypeptide comprises an amino acid sequence as set forth in SEQ ID NO: 4, 11 or 15.

The fusion polypeptide of the present disclosure may have an ability to promote growth of cells expressing FGF receptors (FGFRs). For example, the fusion polypeptide of the present disclosure may have a mitogenic effect on cells expressing FGFRs. In some cases, the ability of the fusion polypeptide to promote growth of cells expressing FGF receptors is comparable to that of FGF 18 (SEQ ID NO:1) and/or FGF 17 (SEQ ID NO: 2). In some embodiments, the mitogenic effect of the fusion polypeptide on cells expressing FGFRs is comparable to that of FGF 18 (SEQ ID NO:1) and/or FGF 17 (SEQ ID NO: 2). In some embodiments, the mitogenic effect of the fusion polypeptide on cells expressing FGFRs is at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1) and/or FGF 17 (SEQ ID NO: 2). For example, the fusion polypeptide of the present disclosure may have an ability to promote growth of cells (e.g., BaF3 cells) expressing FGFR3c-1c at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1).

The cells expressing FGFRs can be a cell or cell line expressing an FGFR selected from a group consisting of FGFR1, FGFR2, FGFR3, FGFR4, an isoform, mutant, or a combination thereof. For example, the FGFR expressed by the cell or cell line may be FGFR1b, FGFR1c, FGFR2b, FGFR2c, FGFR3b, FGFR3c, FGFRdelt4, and/or a splicing variant thereof (e.g., FGFR1-IIIb, FGFR1-IIIc, FGFR2-IIIb, FGFR2-IIIc, FGFR3-IIIb, FGFR3-IIIc, etc). In some embodiments, the FGFR expressed by the cell or cell line may be a chimeric receptor comprising one or more domains of a first FGFR or an isoform thereof and one or more domains of a second FGFR or an isoform thereof. For example, the FGFR expressed by the cell or cell line may be a chimeric receptor selected from FGFR3b-1c (comprising ectodomain of FGFR3b fused to transmembrane and cytoplasmic domains of FGFR1c), FGFR3c-1c (comprising ectodomain of FGFR3c fused to transmembrane and cytoplasmic domains of FGFR1c), FGFR4-1c (comprising ectodomain of FGFR4 fused to transmembrane and cytoplasmic domains of FGFR1c), and FGFRdelta4-1c (comprising ectodomain of FGFRdelta4 fused to transmembrane and cytoplasmic domains of FGFR1c). In some embodiments, the FGFRs may be human FGFRs.

The ability of the fusion polypeptide to promote cell growth or the mitogenic effect of the fusion polypeptide on cells expressing FGFRs may be selective based on the specific one or more FGFRs expressed by the cell. For example, the fusion polypeptide may have such an ability or effect only on cells expressing FGFR3, FGFR3c, FGFR3c-1c, FGFR3b, FGFR3-IIIc, FGFR3-IIIb, FGFR1c, FGFR2c, FGFR4-1c, or FGFRdelta4-1c. In some cases, the fusion polypeptide of the present disclosure may demonstrate potent mitogenic effect on cells expressing one or more of the FGFRs selected from FGFR3, FGFR3c, FGFR3c-1c, FGFR3b, FGFR3-IIIc, FGFR3-IIIb, FGFR1c, FGFR2c, FGFR4-1c, or FGFRdelta4-1c when administered at low concentration (e.g., when applied in vitro to the cells, e.g., to BaF3 cells or other mammalian cells or cell lines). The low concentration as used herein may be a concentration of the fusion polypeptide of less than about 1 μg/ml, 100 ng/ml, 90 ng/ml, 80 ng/ml, 70 ng/ml, 60 ng/ml, 50 ng/ml, 40 ng/ml, 30 ng/ml, 29 ng/ml, 28 ng/ml, 27 ng/ml, 26 ng/ml, 25 ng/ml, 24 ng/ml, 23 ng/ml, 22 ng/ml, 21 ng/ml, 20 ng/ml, 19 ng/ml, 18 ng/ml, 17 ng/ml, 16 ng/ml, 15 ng/ml, 14 ng/ml, 13 ng/ml, 12 ng/ml, 11 ng/ml, 10 ng/ml, 9 ng/ml, 8 ng/ml, 7 ng/ml, 6 ng/ml, 5 ng/ml, 4 ng/ml, 3 ng/ml, 2 ng/ml, 1.5 ng/ml, 1 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, or 0.1 ng/ml. In some embodiments, the low concentration as used herein may be a concentration of the fusion polypeptide of less than about 100 ng/ml, 90 ng/ml, 80 ng/ml, 70 ng/ml, 60 ng/ml, 50 ng/ml, 40 ng/ml, 30 ng/ml, 29 ng/ml, 28 ng/ml, 27 ng/ml, 26 ng/ml, 25 ng/ml, 24 ng/ml, 23 ng/ml, 22 ng/ml, 21 ng/ml, 20 ng/ml, 19 ng/ml, 18 ng/ml, 17 ng/ml, 16 ng/ml, 15 ng/ml, 14 ng/ml, 13 ng/ml, 12 ng/ml, 11 ng/ml, 10 ng/ml, 9 ng/ml, 8 ng/ml, 7 ng/ml, 6 ng/ml, 5 ng/ml, 4 ng/ml, 3 ng/ml, or 2 ng/ml. In some embodiments, the low concentration as used herein may be a concentration of the fusion polypeptide of about 0.1 ng/ml to 100 ng/ml, e.g., 1 ng/ml to 100 ng/ml, 2 ng/ml to 100 ng/ml, 3 ng/ml to 100 ng/ml, 4 ng/ml to 100 ng/ml, 5 ng/ml to 100 ng/ml, 6 ng/ml to 100 ng/ml, 7 ng/ml to 100 ng/ml, 8 ng/ml to 100 ng/ml, 9 ng/ml to 100 ng/ml, 10 ng/ml to 100 ng/ml, 11 ng/ml to 100 ng/ml, 12 ng/ml to 100 ng/ml, 13 ng/ml to 100 ng/ml, 14 ng/ml to 100 ng/ml, 15 ng/ml to 100 ng/ml, 16 ng/ml to 100 ng/ml, 17 ng/ml to 100 ng/ml, 18 ng/ml to 100 ng/ml, 19 ng/ml to 100 ng/ml, 20 ng/ml to 100 ng/ml, 21 ng/ml to 100 ng/ml, 22 ng/ml to 100 ng/ml, 23 ng/ml to 100 ng/ml, 24 ng/ml to 100 ng/ml, 25 ng/ml to 100 ng/ml, 26 ng/ml to 100 ng/ml, 27 ng/ml to 100 ng/ml, 28 ng/ml to 100 ng/ml, 29 ng/ml to 100 ng/ml, 30 ng/ml to 100 ng/ml, 40 ng/ml to 100 ng/ml, 50 ng/ml to 100 ng/ml, 60 ng/ml to 100 ng/ml, 70 ng/ml to 100 ng/ml, 80 ng/ml to 100 ng/ml, or 90 ng/ml to 100 ng/ml.

The fusion polypeptide of the present disclosure may have an ability to stimulate chondrocyte cell proliferation in vivo and/or in vitro, in some cases, such an ability is comparable to that of FGF18 (e.g., human FGF18) and/or FGF17 (e.g., human FGF17). The chondrocyte cell may be human articular chondrocytes. In some embodiments, the ability of the fusion polypeptide to stimulate chondrocyte cell proliferation is at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1) and/or FGF 17 (SEQ ID NO: 2). For example, the fusion polypeptide of the present disclosure may have an ability to stimulate chondrocyte cell proliferation at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1).

The fusion polypeptide of the present disclosure may have an ability to increase proteoglycan synthesis in chondrocyte cells, in vivo and/or in vitro (for example, as revealed by Safranin 0 staining). In some cases, such an ability is comparable to that of FGF18 (e.g., human FGF18) and/or FGF17 (e.g., human FGF17). The chondrocyte cells may be human articular chondrocytes. In some embodiments, the ability of the fusion polypeptide to increase proteoglycan synthesis in chondrocyte cells is at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1) and/or FGF 17 (SEQ ID NO: 2). For example, the fusion polypeptide of the present disclosure may have an ability to increase proteoglycan synthesis in chondrocyte cells at a level that is at least 20%, 30%, 40%, 50%, 60%, 70%, 80%, 90%, 100%, 150%, 200%, 250%, 300%, 350%, 400%, 450%, or 500% of that of FGF18 (SEQ ID NO: 1).

The present disclosure also provides host cells expressing the fusion proteins disclosed herein. A host cell includes an individual cell, cell culture, or cell line. Host cells include progeny of a single host cell. A host cell can be transfected with a heterologous sequence including vectors of the present disclosure. Host cells may be prokaryotic or eukaryotic, such as bacterial cells, fungal cells, animal cells, insect cells, plant cells and the like. Examples of bacterial host cells include microorganisms belonging to the genus *Escherichia, Serratia, Bacillus, Brevibacterium, Corynebacterium, Microbacterium, Pseudomonas* and the like. For example, bacterial host cells may include, but not be limited to, *Escherichia coli* XL1-Blue, XL2-Blue, DH1, MC1000, KY3276, W1485, JM109, HB101, No. 49, W3110, NY49, G1698, BL21 or TB1. Other bacterial host cells may include, but not be limited to, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 13869, *Corynebacterium acetoacidophilum* ATCC 13870, *Microbacterium ammoniaphilum* ATCC 15354, *Pseudomonas putida, Pseudomonas* sp. D-0110 and the like.

Yeast host cells may include microorganisms belonging to the genus *Kluyveromyces, Trichosporon, Saccharomyces, Schizosaccharomyces, Schwanniomyces, Pichia, Candida* and the like, such as *Saccharomyces cerevisiae, Schizosaccharomyces pombe, Kluyveromyces lactis, Trichosporon pullulans, Schwanniomyces alluvius, Candida utilis* and the like.

Examples of eukaryotic cells may include animal cells such as mammalian cells. For example, host cells may include, but are not limited to, Chinese hamster ovary cells (CHO) or monkey cells, such as COS cells, HepG2 cells, A549 cells, BaF3 cell, and any other cells that are available through ATCC or other depositories.

The host cells of the present disclosure may be grown in cultures, and in any apparatus that may be used to grow cultures, including fermenters. They may be grown as monolayers or attached to a surface. Alternatively, the host cells may be grown in suspension. The cells can be grown in a culture medium that is serum-free. The media can be a commercially available media, such as, but not limited to, Opti-CHO (Invitrogen, Catalogue #12681) supplemented with glutamine, such as 8 mM L-glutamine; RPMI 1640 medium, supplemented with 10% bovine calf serum, 10.5 ng/ml mIL-3 and L-glutamine; or 5% FCS medium.

The host cells of the present disclosure may comprise a heterologous sequence to effect expression of the subject fusion polypeptides. The heterologous sequence may comprise a vector, which is a nucleic acid molecule, preferably self-replicating, which transfers an inserted nucleic acid molecule into and/or between host cells. Vectors may include those that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An expression vector is a polynucleotide which, when introduced into an appropriate host cell, can be transcribed and translated into a polypeptide(s).

The heterologous sequence encoding a fusion protein of the present disclosure can be expressed by a single or multiple vectors. The nucleic acid sequences can be arranged in any order in a single operon, or in separate operons that are placed in one or multiple vectors. Where desired, two or more expression vectors can be employed, each of which contains one or more heterologous sequences operably linked in a single operon. Linked refers to the joining together of two more chemical elements or components, by whatever means including chemical conjugation or recombinant means. Operably-linked refers to a juxtaposition wherein the components so described are in a relationship permitting them to function in their intended manner. For instance, a promoter sequence is linked, or operably linked, to a coding sequence if the promoter sequence drives transcription of the coding sequence. The subject vectors can stay replicable episomally, or as an integral part of the host cell genome.

The heterologous sequences of the present disclosure can be under the control of a single regulatory element. In some cases, the heterologous nucleic acid sequences are regulated by a single promoter. In other cases, the heterologous nucleic acid sequences are placed within a single operon. In still other cases, the heterologous nucleic acid sequences are placed within a single reading frame.

Preparation of the subject nucleic acids can be carried out by a variety of routine recombinant techniques and synthetic procedures. Standard recombinant DNA and molecular cloning techniques are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M L. Bennan, and L. W. Enquist, *Experiments with Gene Fusions*, Cold Spring Harbor Laboratory, Cold Spring Harbor, N.Y. (1984) and by Ausubel, F. M et al., *Current Protocols in Molecular Biology*, pub. by Greene Publishing Assoc. and Wiley-Interscience (1987). Briefly, the subject nucleic acids can be prepared genomic DNA fragments, cDNAs, and RNAs, all of which can be extracted directly from a cell or recombinantly produced by various amplification processes including but not limited to PCR and rt-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (for example, Matteuci et al., *Tet. Lett.* 521:719 (1980); U.S. Pat. No. 4,500,707 to Caruthers et al.; and U.S. Pat. Nos. 5,436,327 and 5,700,637 to Southern et al.).

Regulatory elements include, for example, promoters and operators, which can also be engineered to increase the expression of one or more heterologous sequences encoding a glycoprotein. A promoter is a sequence of nucleotides that initiates and controls the transcription of a nucleic acid sequence by an RNA polymerase enzyme. An operator is a sequence of nucleotides adjacent to the promoter that functions to control transcription of the desired nucleic acid sequence. The operator contains a protein-binding domain where a specific repressor protein can bind. In the absence of a suitable repressor protein, transcription initiates through the promoter. In the presence of a suitable repressor protein, the repressor protein binds to the operator and thereby inhibits transcription from the promoter.

In some embodiments of the present disclosure, promoters used in expression vectors are inducible. In other embodiments, the promoters used in expression vectors are constitutive. In some embodiments, one or more nucleic acid sequences are operably linked to an inducible promoter, and one or more other nucleic acid sequences are operably linked to a constitutive promoter. Non-limiting examples of suitable promoters for use in eukaryotic host cells include, but are not limited to, a CMV immediate early promoter, an HSV thymidine kinase promoter, an early or late SV40 promoter, LTRs from retroviruses, and a mouse metallothionein-I promoter.

The genes in the expression vector typically will also encode a ribosome binding site to direct translation (that is, synthesis) of any encoded mRNA gene product. Other regulatory elements that may be used in an expression vector include transcription enhancer elements and transcription terminators. See, for example, Bitter et al., *Methods in Enzymology,* 153:516-544 (1987).

An expression vector may be suitable for use in particular types of host cells and not others. One of ordinary skill in the art, however, can readily determine through routine experimentation whether a particular expression vector is suited for a given host cell. For example, the expression vector can be introduced into the host organism, which is then monitored for viability and expression of any genes contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other transformation methods may include microinjection, DEAE dextran mediated transformation, and heat shock in the presence of lithium acetate. Lipid complexes, liposomes, and dendrimers may also be employed to transfect the host cells.

Upon introduction of the heterologous sequence into a host cell, a variety of methods can be practiced to identify the host cells into which the subject vectors have been introduced. One exemplary selection method involves subculturing individual cells to form individual colonies, followed by testing for expression of the desired protein product. Another method entails selecting host cells containing the heterologous sequence based upon phenotypic traits conferred through the expression of selectable marker genes contained within the expression vector. Those of ordinary skill can identify genetically modified host cells using these or other methods available in the art.

For example, the introduction of various heterologous sequences of the disclosure into a host cell can be confirmed by methods such as PCR, Southern blot or Northern blot hybridization. For example, nucleic acids can be prepared from the resultant host cells, and the specific sequences of interest can be amplified by PCR using primers specific for the sequences of interest. The amplified product is subjected to agarose gel electrophoresis, polyacrylamide gel electrophoresis or capillary electrophoresis, followed by staining with ethidium bromide, SYBR Green solution or the like, or detection of DNA with a UV detection. Alternatively, nucleic acid probes specific for the sequences of interest can be employed in a hybridization reaction. The expression of a specific gene sequence can be ascertained by detecting the corresponding mRNA via reveres-transcription coupled PCR, Northern blot hybridization, or by immunoassays using antibodies reactive with the encoded gene product. Exemplary immunoassays include but are not limited to ELISA, radioimmunoassays, and sandwich immunoassays.

Furthermore, the introduction of various heterologous sequences of the disclosure into a host cell can be confirmed by the enzymatic activity of an enzyme that the heterologous sequence encodes. The enzyme can be assayed by a variety of methods known in the art. In general, the enzymatic activity can be ascertained by the formation of the product or conversion of a substrate of an enzymatic reaction that is under investigation. The reaction can take place in vitro or in vivo.

In another aspect, the present disclosure provides a method of producing a fusion polypeptide to achieve desired pharmacokinetic, pharmacologic or pharmaceutical properties. In some cases, the fusion polypeptide can be produced by expressing a vector in a cell under conditions suitable for protein expression.

The suitable conditions for protein expression, including but not limited to factors such as incubation time, temperature, and medium, may be dependent on cell type and will be readily determined by one of ordinary skill in the art.

Methods of Treatment

In one aspect, the present disclosure provides methods of using the fusion polypeptides of the present disclosure to treat disease conditions in a mammal, including but not limited to conditions implicated by FGF receptor (e.g., FGFR1, FGFR2, FGFR3 (e.g., FGFR3b and/or FGFR3c), and/or FGFR4) malfunction.

The present disclosure also provides use of the fusion polypeptides of the present disclosure for the manufacture/preparation of a pharmaceutical composition for treating disease conditions in a mammal, including but not limited to conditions implicated by FGF receptor (e.g., FGFR1, FGFR2, FGFR3 (e.g., FGFR3b and/or FGFR3c), and/or FGFR4) malfunction. For example, the disease condition may be a cartilage defect. In some cases, the cartilage defect can be osteoarthritis or degenerative disc disease. In other examples, the cartilage defect can be cartilage injury. In some embodiments, said treating a disease condition is cartilage repair, e.g., cartilage microfracture surgery.

In some cases, the present disclosure provides a method of treating a cartilage defect in a mammal in need thereof, comprising administering to the mammal a therapeutically effective amount of a fusion polypeptide of the disclosure. In some examples, the cartilage defect can be osteoarthritis or degenerative disc disease. In other examples, the cartilage defect can be cartilage injury. In some embodiments, said treating a cartilage defect is cartilage repair, e.g., cartilage microfracture surgery.

In some cases, the mammal is a human. In other cases, the mammal can be a mouse, a rat, a cat, a dog, a rabbit, a pig, a sheep, a horse, a bovine, a goat, a gerbil, a hamster, a guinea pig, a monkey or any other mammal. Many such mammals may be subjects that are known to the art as preclinical models for certain diseases or disorders, including solid tumors and/or other cancers (e.g., Talmadge et al., 2007 Am. J. Pathol. 170:793; Kerbel, 2003 Canc. Biol. Therap. 2(4 Suppl 1):S134; Man et al., 2007 Canc. Met. Rev. 26:737; Cespedes et al., 2006 Clin. TransL Oncol. 8:318).

In another aspect, the disclosure provides methods of using the fusion polypeptides of the present disclosure to treat disease conditions in a mammal wherein the fusion polypeptides may be formulated or administered in conjunction with a second agent. In some cases, the second agent can be hyaluronic acid. In other cases, the second agent can be an agent that acts to relieve the symptoms of conditions such as osteoarthritis, degenerative disc disease, and the other diseases described herein. These agents may include non-steroidal anti-inflammatory drugs (NSAIDs), e.g., acetylsalicylic acid; ibuprofen; naproxen; indomethacin; nabumetone; tolmetin, etc. Corticosteroids are used to reduce inflammation and suppress activity of the immune system. The most commonly prescribed drug of this type is Prednisone. Paracetamol may also be effective in some patients with osteoarthritis. Anticoagulants may be employed to prevent blood from clotting rapidly. They range from aspirin at very low dose which prevents platelets from sticking, to heparin/coumadin.

Pharmaceutical Compositions

A pharmaceutical composition of the disclosure typically contains an active ingredient (e.g., a fusion polypeptide, a PEG-modified fusion polypeptide) of the present disclosure or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants. Described below are non-limiting exemplary pharmaceutical compositions and methods for preparing the same.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition can further comprise a fusion polypeptide and/or a PEG-modified fusion peptide according to the disclosure as an active ingredient and may include a conventional pharmaceutical carrier or excipient. Further, it may include other medicinal or pharmaceutical agents, carriers, adjuvants, etc.

Exemplary parenteral administration forms include, but not limited to, solutions or suspensions of active polypeptide and/or PEG-modified polypeptide in sterile aqueous solutions, for example, aqueous propylene glycol or dextrose solutions. Such dosage forms can be suitably buffered with salts such as histidine and/or phosphate, if desired.

In some cases, the disclosure provides a pharmaceutical composition for injection containing a polypeptide or a PEG-modified polypeptide of the present disclosure and a pharmaceutical excipient suitable for injection. Components and amounts of agents in the compositions are as described herein.

The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

In Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the polypeptide or PEG-modified polypeptide of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

In some cases, the disclosure provides a pharmaceutical composition for oral administration containing a fusion polypeptide or a PEG-modified fusion polypeptide of the disclosure, and a pharmaceutical excipient suitable for oral administration.

In some cases, the disclosure provides a solid pharmaceutical composition for oral administration containing: (i) an effective amount of a polypeptide or a PEG-modified polypeptide of the disclosure; optionally (ii) an effective amount of a second agent; and (iii) a pharmaceutical excipient suitable for oral administration. In some embodiments, the composition further contains: (iv) an effective amount of a third agent.

In some cases, the pharmaceutical composition may be a liquid pharmaceutical composition suitable for oral consumption. Pharmaceutical compositions of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

This disclosure further encompasses anhydrous pharmaceutical compositions and dosage forms comprising an active ingredient, since water can facilitate the degradation of some polypeptides. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

A fusion polypeptide can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the disclosure to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EXAMPLES

The examples and preparations provided below further illustrate and exemplify the fusion polypeptides of the present disclosure and methods of using and preparing thereof. It is to be understood that the scope of the present disclosure is not limited in any way by the scope of the following examples and preparations.

Example 1: Cloning and Expression of FGF18/FGF17 Fusion Polypeptides

Polypeptides and fusion polypeptides of SEQ ID NO: 1, 2, 3, 4, 5, 6, 7, 8, 9, 10, 11, 12, 13, 14, 15, and 16 were designed and expressed in *E. coli*. Briefly, genes encoding the fusion polypeptides were inserted into the expression vector pET11a between the NdeI and BamH1 restriction sites and expression was conducted under control of the phage T7 promotor. The vectors were transformed into *E. coli* BL21 (DE3). The cells were grown in LB media supplemented with 100 μg/ml of ampicillin to $OD_{450}$ of 0.4-0.6. Expressions were induced by addition of 1 mM IPTG for 12 hours at 37° C. Cells were harvested by centrifugation, suspended in PBS, and sonicated. The cell homogenates were centrifuged. SDS-PAGE analysis was performed to demonstrate that fusion polypeptides, for example SEQ ID NO: 1, 2, 4, 11 and 15 were successfully expressed in the insoluble inclusion body fractions (FIG. 1).

Example 2: Refolding and Purification of FGF18/FGF17 Fusion Polypeptides

Figure 2:
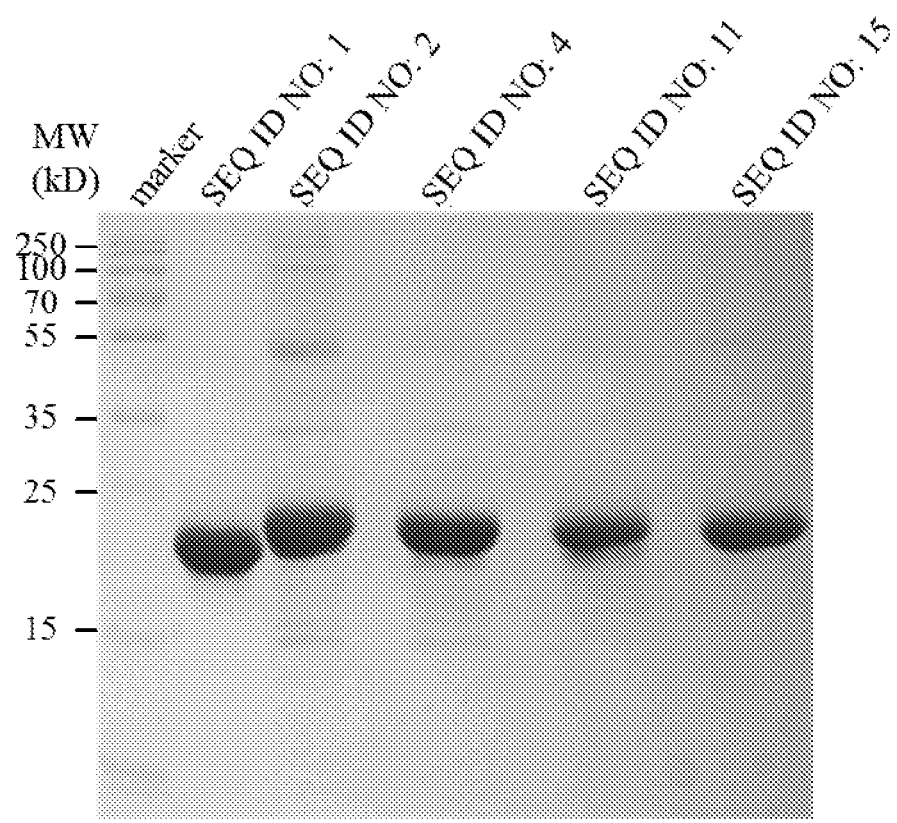
FIG. 2 illustrates the SDS-PAGE analysis following the refolding and purification of fusion polypeptides and their reference polypeptides (SEQ ID NO: 1, 2, 4, 11, and 15) using the methods of the present disclosure.

Polypeptides and fusion polypeptides of SEQ ID NO: 1, 2, 3, 4, 5, 6, 7, 8, 9, 10, 11, 12, 13, 14, 15, and 16 were refolded and purified as follows. Following expression, the cells were harvested by centrifuge, re-suspended in PBS and homogenized. The homogenate was then centrifuged at 4000 rpm for 20 minutes at 4° C. The pellet containing the polypeptides and fusion polypeptides was obtained after discarding the supernatant. The inclusion body was then washed in PBS contains 2M urea, centrifuged at 4000 rpm for 20 minutes at 4° C. The washed inclusion body was solubilized in 50 mM Tris, 6M guanidine hydrochloride, 10 mM DTT pH8.0 at a v/v ratio of 1/10. Solubilization was carried out for 3-4 hours at room temperature. The solubilized sample was then clarified by centrifugation. The GuaHCl/polypeptide (or fusion polypeptide) solution was then diluted drop-wise into a refolding buffer containing 50 mMTris-HCl, 4 mM cysteine, 2 mMDTT, 2 MUrea, 120 mM NaCl, pH8.0 at a v/v ratio of 1/20 and stirred overnight at 4° C. The refolded sample was clarified by filtration and then captured on a cation exchange column, e.g., SP.BB (GE Healthcare), at pH8.0, and the bound (fusion) polypeptide was eluted with an increasing linear gradient from 0 to 1M sodium chloride in 20 mM PB, pH8.0. The eluted pool was then ultra-filtrated to a small volume. Superdex-75 (GE healthcare) column was then employed to purify the desired polypeptide. The column was equipped with PBS or 20 mM Hepes, 140 mM NaCl, pH7.0. The sample volume loaded on gel filtration column is less than 3% column volume. The elution peak containing the desired polypeptide was pooled and glycerol was added to a final concentration of 10% (as shown in FIG. 2). The sample was then stored at −20° C.

Example 3: Construction of FGFR Expression Vectors

FGFR1b, FGFR1c, FGFR2b, and FGFR2c expression vectors pcDNA3-FGFR1-IIIb, pcDNA3-FGFR1-IIIc, pcDNA3-FGFR2-IIIb and pcDNA3-FGFR2-IIIc were generated as following. Full-length human FGFR1-IIIb (FJ809917.1), FGFR1-IIIc (NM_023110.2), FGFR2-IIIb (NM_022970.3), and FGFR2-IIIc (NM_000141.4) genes were synthesized and then cloned into BamHI/NotI restriction sites of pcDNA3 vector from Taihe Biotechnology Co., LTD (Beijing, China). The vector pcDNA3-FGFR3-IIIb/R1c expresses a chimeric receptor bearing the ectodomain of human FGFR3b fused to the transmembrane and cytoplasmic domains of human FGFR1c. The vector pcDNA3-FGFR3-IIIc/R1c expresses a chimeric receptor bearing the ectodomain of human FGFR3c fused to the transmembrane and cytoplasmic domains of human FGFR1c. The vector pcDNA3-FGFR4/R1c expresses a chimeric receptor bearing the ectodomain of human FGFR4 fused to the transmembrane and cytoplasmic domains of human FGFR1c. The vector pcDNA3-FGFRA4/RIC expresses a chimeric receptor bearing the ectodomain of human FGFRA4 (a truncated form of human FGFR4) fused to the transmembrane and cytoplasmic domains of human FGFR1c.

Example 4: DNA Transfection and Cell Selection

BaF3 cells were grown in RPMI 1640 medium, supplemented with 10% bovine calf serum, 10.5 ng/ml mIL-3 and L-glutamine. These cells were transfected by electroporation (1000 UF, 220V) with various FGFR expression vectors constructed in Example 3 and selected with G418 (600 μg/ml) plus mIL-3 conditioned medium, thereby obtaining cells expressing the FGFRs.

Example 5: Proliferation Assay

BaF3 cells transfected with the FGFR expressing vectors (as obtained in Example 4) were selected with G418 for 10 days, then washed for 3 times with Phosphate buffer saline (PBS). The cells ($5\times10^4$ per well) were plated in 96-well plates (Corning Life Sciences, MA). Increasing concentration of the fusion polypeptide of the present disclosure, reference polypeptide and/or control polypeptide, together with 2 μg/ml heparin, were added in a total volume of 200 μl. 96 hours later, 100 μl luciferase detect reagent Cell titer glo (Promega Corporation, Madison, Wis. USA) was added to all wells and incubate at room temperature for 5 mins. Then read on a multiplate reader. EC50 was calculated with prism5.

Example 6: Mitogenic Assay

Human articular chondrocytes were obtained from Lonza Walkersville, Inc. (Walkersville, Md.) and cultured according to the manufacturer's instructions. Human articular chondrocytes were plated in 96-well plates at a density of 10,000 cells per 96-well in 5% FCS medium and incubated at 37° C. 5% CO overnight. Then the culture medium was replaced with serum free medium. After 4 days, the media was changed to serum-free media containing 0.1% BSA. The fusion polypeptide of the present disclosure, reference polypeptide and/or control polypeptide were added to the wells after an additional 48 hours of culturing. The cell numbers were not evaluated with cell titer glo reagent until after culturing for an additional 4 days.

Example 7: Micromass Cultures with Chondrocytes

Micromass cultures were established from human articular chondrocytes. These cultures were grown in CBM with 5% FCS either in the presence or absence of 1 μg/ml of the fusion polypeptide of the present disclosure, reference polypeptide and/or control polypeptide. After 4 days, the cultures were fixed and stained with Safranin.

Example 8: Proliferation of BaF3 Cells Transfected with FGFR1b by FGF18/FGF17 Fusion Polypeptides The activities of the FGF18/FGF17 fusion polypeptides were assessed in BaF3/FGFR1b proliferation assay. Specifically, BaF3 cells were grown in RPMI 1640 medium, supplemented with 10% bovine calf serum, 2 ng/ml mIL-3 and L-glutamine. These cells were transfected by electroporation (1000 UF, 140V) with pcDNA3-FGFR1-IIIb, and selected with G418 (600 μg/ml) and FGF1 plus heparin (50 μg/ml) in the absence of IL-3. This procedure yielded BaF3 cell colonies expressing FGFR1b.

Figure 3:
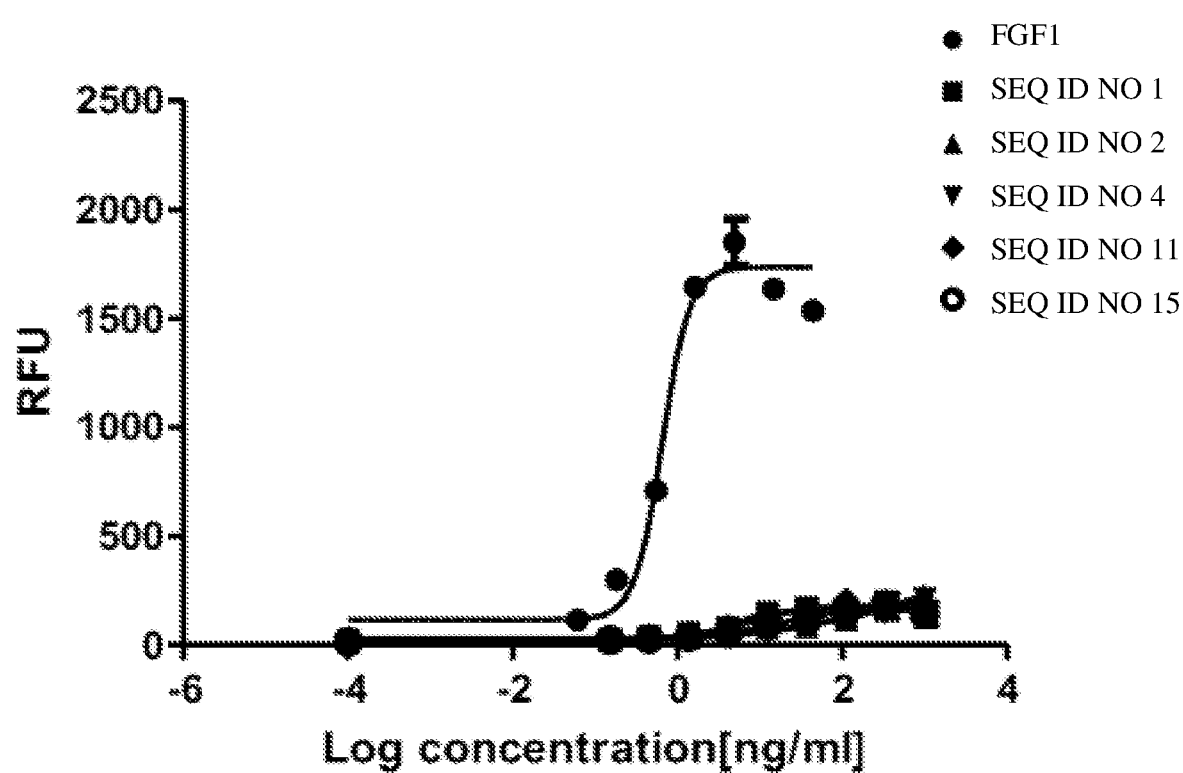
FIG. 3 illustrates the dose-dependent proliferation of BaF3/FGFR1b cells at 96 hours after treatment with positive control (FGF1), reference polypeptides (SEQ ID NO: 1 and 2), and fusion polypeptides (SEQ ID NO: 4, SEQ ID NO: 11, and SEQ ID NO: 15).

BaF3/FGFR1b cells were washed 3 times with PBS. The cells ($5\times10^4$ per well) were plated in 96-well plates. Appropriate FGFs and fusion polypeptides of the present disclosure, together with heparin, were added in a total volume of 200 μl. 100 μl Cell Titer-Glo (Promega) was added to the 96-well plate after 96 hours and incubated at room temperature for 10 min. Luminescence was monitored by multiplate reader synergyII (Bioteck). The background signal from wells without any growth factor was subtracted from the values obtained in its presence. All treatments were performed in triplicates (FIG. 3). FGF1 served as positive control. As can be seen in FIG. 3, FGF 1 shows potent mitogenic effect in FGFR1b transfected BaF3 cells while FGF18, FGF17b and the fusion polypeptides shows very little, if any at all, this activity.

Example 9: Proliferation of BaF3 Cells Transfected with FGFR1c by FGF18/FGF17 Fusion Polypeptides The activities of the FGF18/FGF17 fusion polypeptides were assessed in BaF3/FGFR1c proliferation assay. Specifically, BaF3 cells were grown in RPMI 1640 medium, supplemented with 10% bovine calf serum, 2 ng/ml mIL-3 and L-glutamine. These cells were transfected by electroporation (1000 UF, 140V) with pcDNA3-FGFR1-IIIc, and selected with G418 (600 μg/ml) and FGF1 plus heparin (50 μg/ml) in the absence of IL-3. This procedure yielded BaF3 cell colonies expressing FGFRκ.

Figure 4:
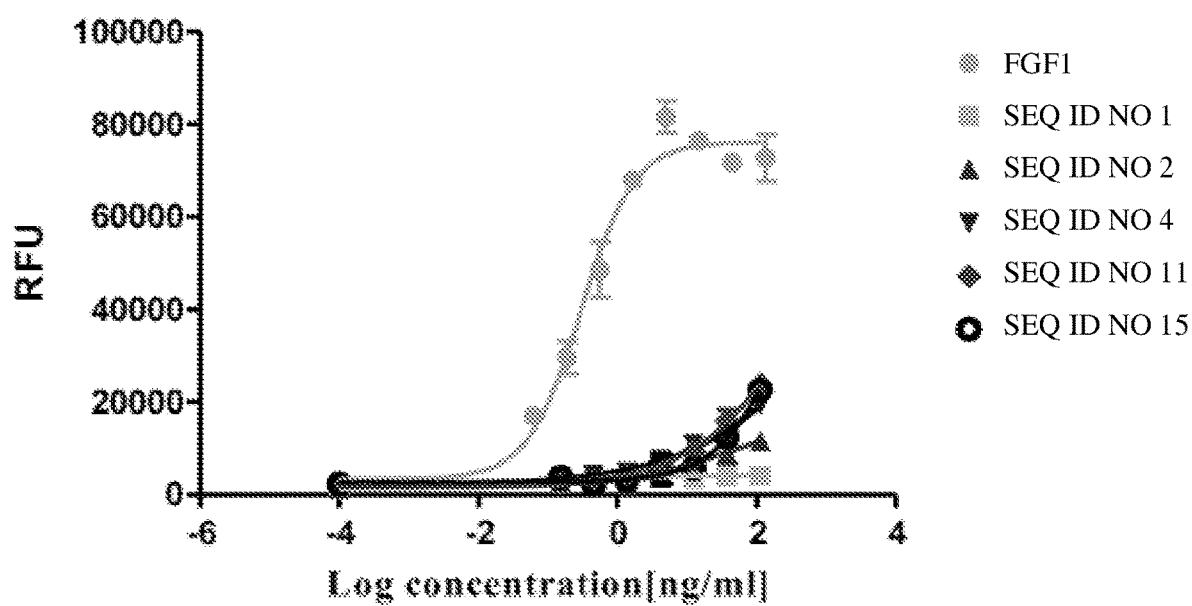
FIG. 4 illustrates the dose-dependent proliferation of BaF3/FGFR1c cells at 96 hours after treatment with positive control (FGF1), reference polypeptides (SEQ ID NO: 1 and 2), and fusion polypeptides (SEQ ID NO: 4, SEQ ID NO: 11, and SEQ ID NO: 15).

BaF3/FGFR1c cells were washed 3 times with PBS. The cells ($5 \times 10^4$ per well) were plated in 96-well plates. Appropriate FGFs and fusion polypeptides of the present disclosure, together with heparin, were added in a total volume of 200 μl. 100 μl Cell Titer-Glo (Promega) was added to the 96-well plate after 96 hours and incubated at room temperature for 10 min. Luminescence was monitored by multiplate reader synergyII (Bioteck). The background signal from wells without any growth factor was subtracted from the values obtained in its presence. All treatments were performed in triplicates (FIG. 4). FGF1 served as positive control. As can be seen in FIG. 4, FGF 1 shows potent mitogenic effect in FGFRκ transfected BaF3 cells while FGF18, FGF17b and the fusion polypeptides only showed some mitogenic activity in high concentration.

Example 10: Proliferation of BaF3 Cells Transfected with FGFR2c by FGF18/FGF17 Fusion Polypeptides The activities of the FGF18/FGF17 fusion polypeptides were assessed in BaF3/FGFR2c proliferation assay. Specifically, BaF3 cells were grown in RPMI 1640 medium, supplemented with 10% bovine calf serum, 2 ng/ml mIL-3 and L-glutamine. These cells were transfected by electroporation (1000 UF, 140V) with pcDNA3-FGFR2-IIIc, and selected with G418 (600 μg/ml) and FGF1 plus heparin (50 μg/ml) in the absence of IL-3. This procedure yielded BaF3 cell colonies expressing FGFR2c.

BaF3/FGFR2c cells were washed 3 times with PBS. The cells ($5 \times 10^4$ per well) were plated in 96-well plates. Appropriate FGFs and fusion polypeptides of the present disclosure, together with heparin, were added in a total volume of 200 μl. 100 μl Cell Titer-Glo (Promega) was added to the 96-well plate after 96 hours and incubated at room temperature for 10 min.

Figure 5:
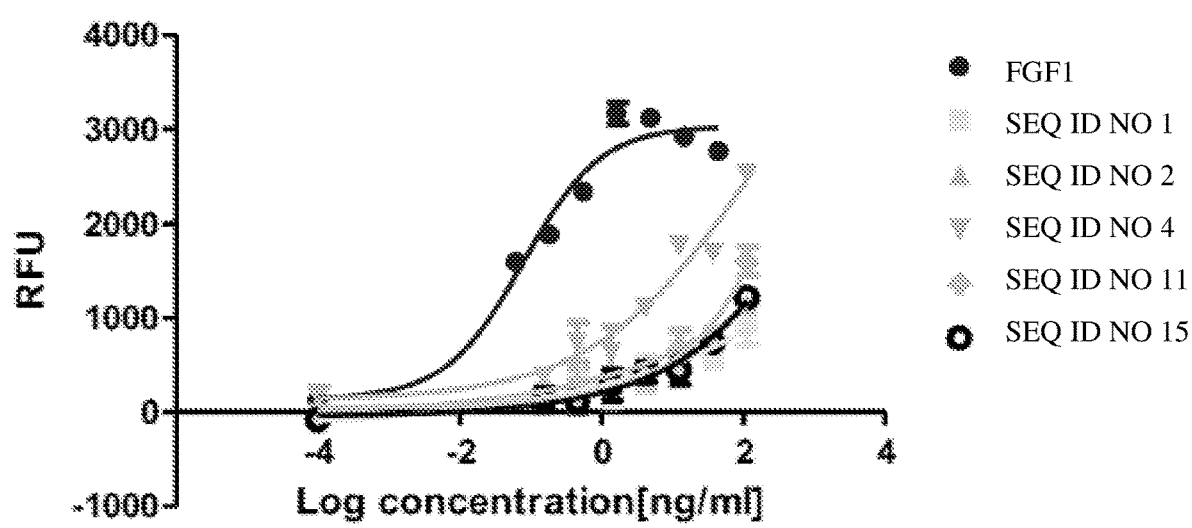
FIG. 5 illustrates the dose-dependent proliferation of BaF3/FGFR2c cells at 96 hours after treatment with positive control (FGF1), reference polypeptides (SEQ ID NO: 1 and 2), and fusion polypeptides (SEQ ID NO: 4, SEQ ID NO: 11, and SEQ ID NO: 15).

Luminescence was monitored by multiplate reader synergyII (Bioteck). The background signal from wells without any growth factor was subtracted from the values obtained in its presence. All treatments were performed in triplicates (FIG. 5). FGF1 served as positive control. As can be seen in FIG. 5, FGF 1 shows potent mitogenic effect in FGFR2c transfected BaF3 cells while FGF18, FGF17b and the fusion polypeptides only showed some mitogenic activity in high concentration.

Example 11: Proliferation of BaF3 Cells Transfected with FGFR3b by FGF18/FGF17 Fusion Polypeptides The activities of the FGF18/FGF17 fusion polypeptides were assessed in BaF3/FGFR3b proliferation assay. Specifically, BaF3 cells were grown in RPMI 1640 medium, supplemented with 10% bovine calf serum, 2 ng/ml mIL-3 and L-glutamine. These cells were transfected by electroporation (1000 UF, 140V) with pcDNA3-FGFR3-IIIb, and selected with G418 (600 μg/ml) and FGF1 plus heparin (50 μg/ml) in the absence of IL-3. This procedure yielded BaF3 cell colonies expressing FGFR3b.

Figure 6:
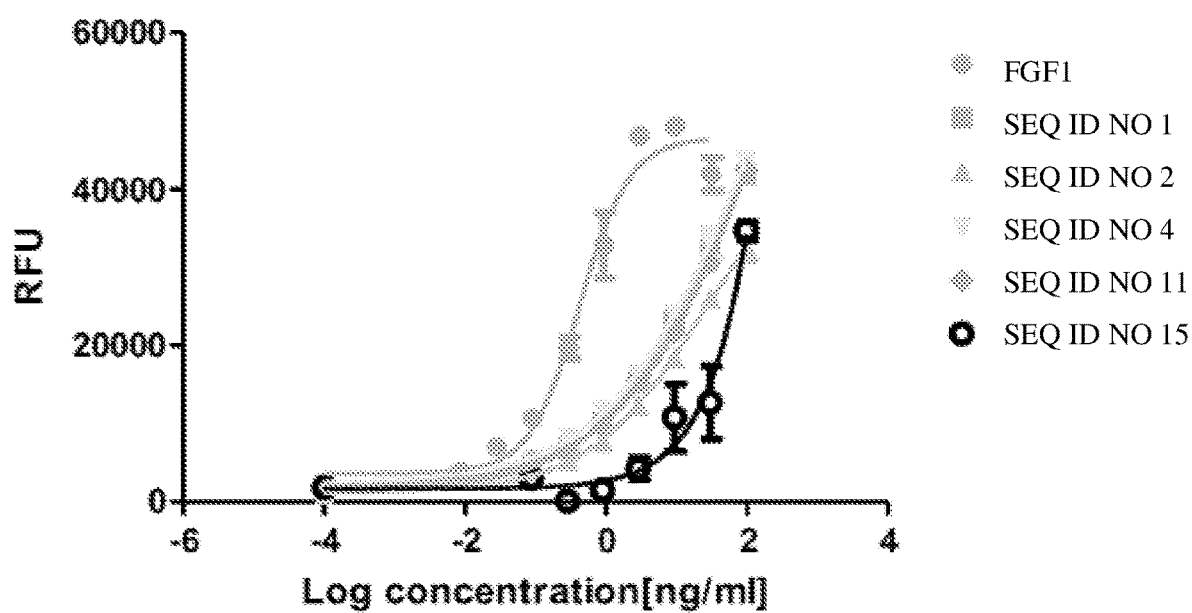
FIG. 6 illustrates the dose-dependent proliferation of BaF3/FGFR3b cells at 96 hours after treatment with positive control (FGF1), reference polypeptides (SEQ ID NO: 1 and 2), and fusion polypeptides (SEQ ID NO: 4, SEQ ID NO: 11, and SEQ ID NO: 15).

BaF3/FGFR3b cells were washed 3 times with PBS. The cells ($5 \times 10^4$ per well) were plated in 96-well plates. Appropriate FGFs and fusion polypeptides of the present disclosure, together with heparin, were added in a total volume of 200 μl. 100 μl Cell Titer-Glo (Promega) was added to the 96-well plate after 96 hours and incubated at room temperature for 10 min. Luminescence was monitored by multiplate reader synergyII (Bioteck). The background signal from wells without any growth factor was subtracted from the values obtained in its presence. All treatments were performed in triplicates (FIG. 6). FGF1 served as positive control. As can be seen in FIG. 6, FGF 1 shows potent mitogenic effect in FGFR3b transfected BaF3 cells while FGF18, FGF17b and the fusion polypeptides only showed some mitogenic activity in high concentration.

Example 12: Proliferation of BaF3 Cells Transfected with FGFR3c-1c by FGF18/FGF17 Fusion Polypeptides The activities of the FGF18/FGF17 fusion polypeptides were assessed in BaF3/FGFR3c-1c proliferation assay. Specifically, BaF3 cells were grown in RPMI 1640 medium, supplemented with 10% bovine calf serum, 2 ng/ml mIL-3 and L-glutamine. These cells were transfected by electroporation (1000 UF, 140V) with pcDNA3-FGFR3-IIIc/R1c, and selected with G418 (600 μg/ml) and FGF1 plus heparin (50 μg/ml) in the absence of IL-3. This procedure yielded BaF3 cell colonies expressing FGFR3c-1c.

Figure 7:
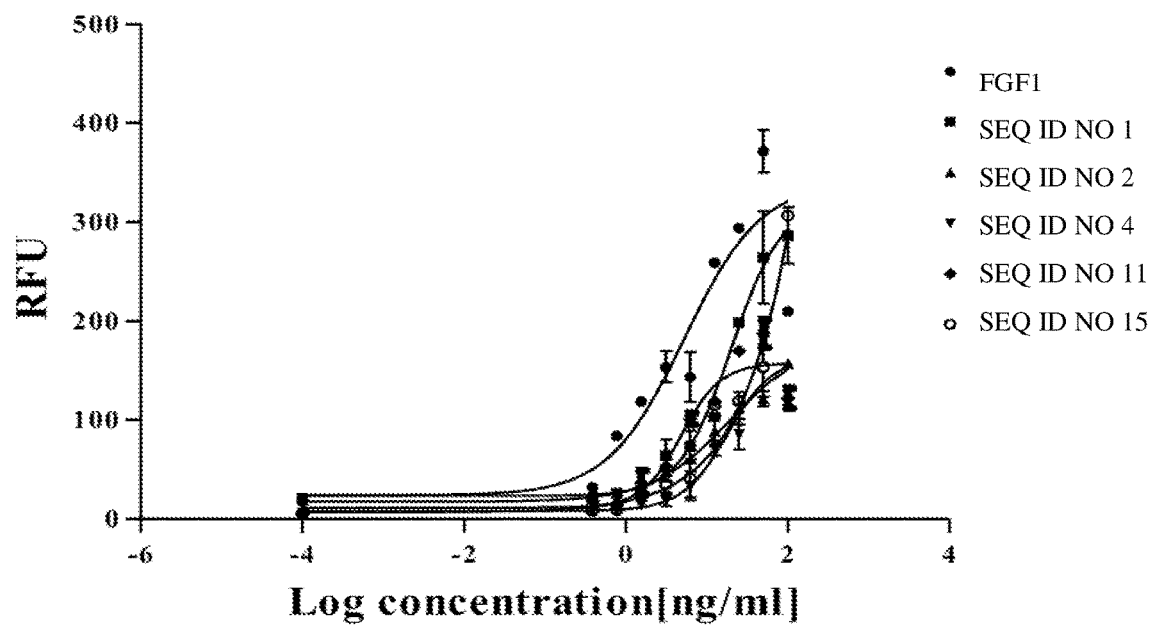
FIG. 7 illustrates the dose-dependent proliferation of BaF3/FGFR3c-1c cells at 96 hours after treatment with positive control (FGF1), reference polypeptides (SEQ ID NO: 1 and 2), and fusion polypeptides (SEQ ID NO: 4, SEQ ID NO: 11, and SEQ ID NO: 15).

BaF3/FGFR3c-1c cells were washed 3 times with PBS. The cells ($5 \times 10^4$ per well) were plated in 96-well plates. Appropriate FGFs and fusion polypeptides of the present disclosure, together with heparin, were added in a total volume of 200 μl. 100 μl Cell Titer-Glo (Promega) was added to the 96-well plate after 96 hours and incubated at room temperature for 10 min. Luminescence was monitored by multiplate reader synergyII (Bioteck). The background signal from wells without any growth factor was subtracted from the values obtained in its presence. All treatments were performed in triplicates (FIG. 7). FGF1 served as positive control. As can be seen in FIG. 7, FGF 1, FGF18, FGF17b and the fusion polypeptides all showed potent mitogenic effect in FGFR3c-1c transfected BaF3 cells.

Example 13: Proliferation of BaF3 Cells Transfected with FGFR4-1c by FGF18/FGF17 Fusion Polypeptides The activities of the FGF18/FGF17 fusion polypeptides were assessed in BaF3/FGFR4-1c proliferation assay. Specifically, BaF3 cells were grown in RPMI 1640 medium, supplemented with 10% bovine calf serum, 2 ng/ml mIL-3 and L-glutamine. These cells were transfected by electroporation (1000 UF, 140V) with pcDNA3-FGFR4/R1c, and selected with G418 (600 μg/ml) and FGF1 plus heparin (50 μg/ml) in the absence of IL-3. This procedure yielded BaF3 cell colonies expressing FGFR4-1c.

Figure 8:
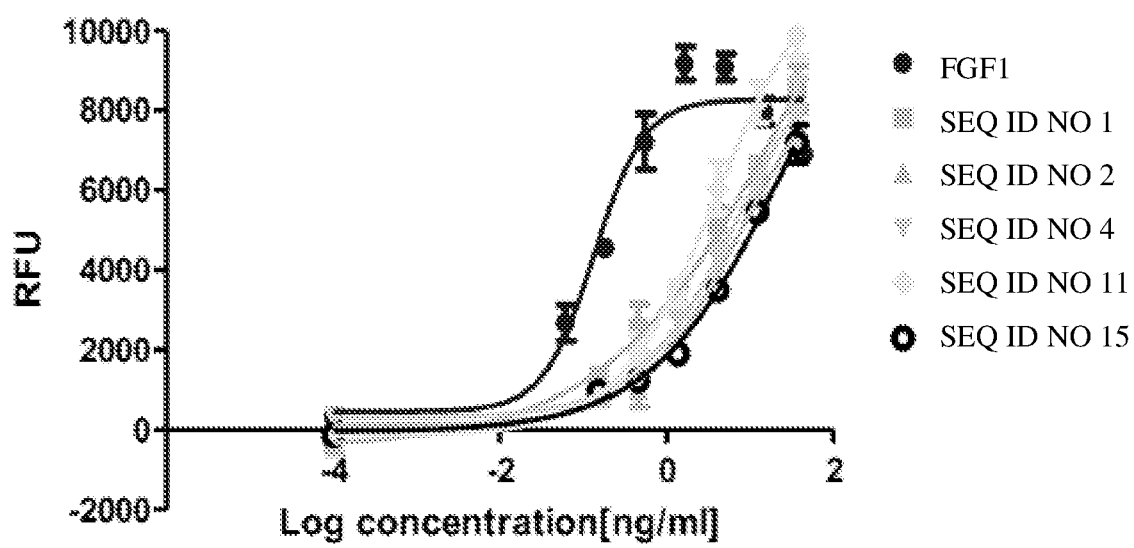
FIG. 8 illustrates the dose-dependent proliferation of BaF3/FGFR4-1c cells at 96 hours after treatment with positive control (FGF1), reference polypeptides (SEQ ID NO: 1 and 2), and fusion polypeptides (SEQ ID NO: 4, SEQ ID NO: 11, and SEQ ID NO: 15).

BaF3/FGFR4-1c cells were washed 3 times with PBS. The cells (5×10⁴ per well) were plated in 96-well plates. Appropriate FGFs and fusion polypeptides of the present disclosure, together with heparin, were added in a total volume of 200 μl. 100 μl Cell Titer-Glo (Promega) was added to the 96-well plate after 96 hours and incubated at room temperature for 10 min. Luminescence was monitored by multiplate reader synergyII (Bioteck). The background signal from wells without any growth factor was subtracted from the values obtained in its presence. All treatments were performed in triplicates (FIG. 8). FGF1 served as positive control. As can be seen in FIG. 8, FGF 1 shows potent mitogenic effect in FGFR4-1c transfected BaF3 cells while FGF18, FGF17b and the fusion polypeptides only showed some mitogenic activity in high concentration.

Example 14: Proliferation of BaF3 Cells Transfected with FGFRdelta4-1c by FGF18/FGF17 Fusion Polypeptides The activities of the FGF18/FGF17 fusion polypeptides were assessed in BaF3/FGFRdelta4-1c proliferation assay. Specifically, BaF3 cells were grown in RPMI 1640 medium, supplemented with 10% bovine calf serum, 2 ng/ml mIL-3 and L-glutamine. These cells were transfected by electroporation (1000 UF, 140V) with pcDNA3-FGFRA4/R1c, and selected with G418 (600 μg/ml) and FGF1 plus heparin (50 μg/ml) in the absence of IL-3. This procedure yielded BaF3 cell colonies expressing FGFRdelta4-1c.

Figure 9:
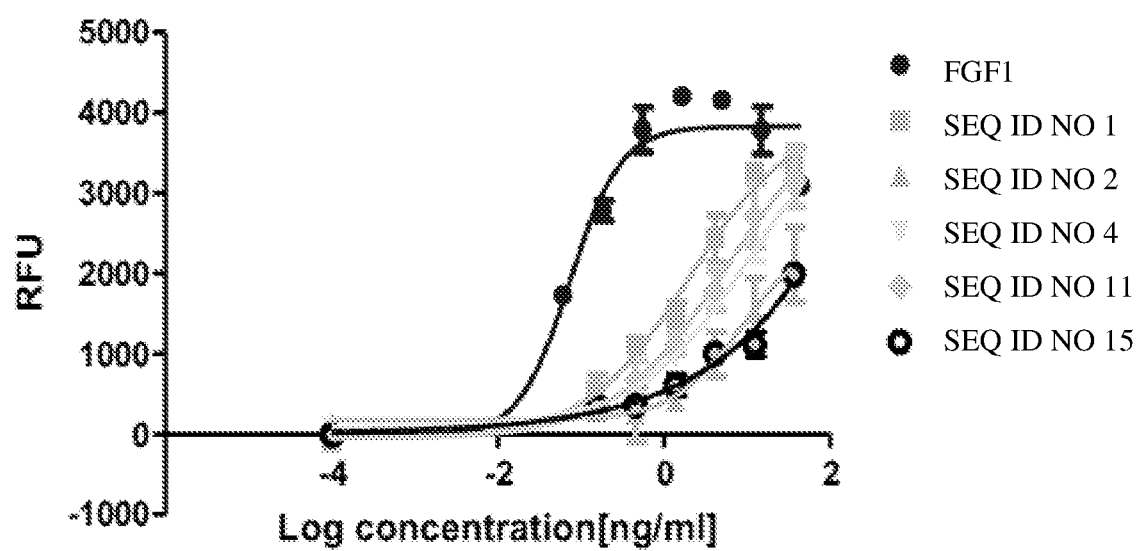
FIG. 9 illustrates the dose-dependent proliferation of BaF3/FGFRdelta4-1c cells at 96 hours after treatment with positive control (FGF1), reference polypeptides (SEQ ID NO: 1 and 2), and fusion polypeptides (SEQ ID NO: 4, SEQ ID NO: 11, and SEQ ID NO: 15).

BaF3/FGFRdelta4-1c cells were washed 3 times with PBS. The cells (5×10⁴ per well) were plated in 96-well plates. Appropriate FGFs and fusion polypeptides of the present disclosure, together with heparin, were added in a total volume of 200 μl. 100 μl Cell Titer-Glo (Promega) was added to the 96-well plate after 96 hours and incubated at room temperature for 10 min. Luminescence was monitored by multiplate reader synergyII (Bioteck). The background signal from wells without any growth factor was subtracted from the values obtained in its presence. All treatments were performed in triplicates (FIG. 9). FGF1 served as positive control. As can be seen in FIG. 9, FGF 1 shows potent mitogenic effect in FGFRdelta4-1c transfected BaF3 cells while FGF18, FGF17b and the fusion polypeptides only showed some mitogenic activity in high concentration.

Figure 10:
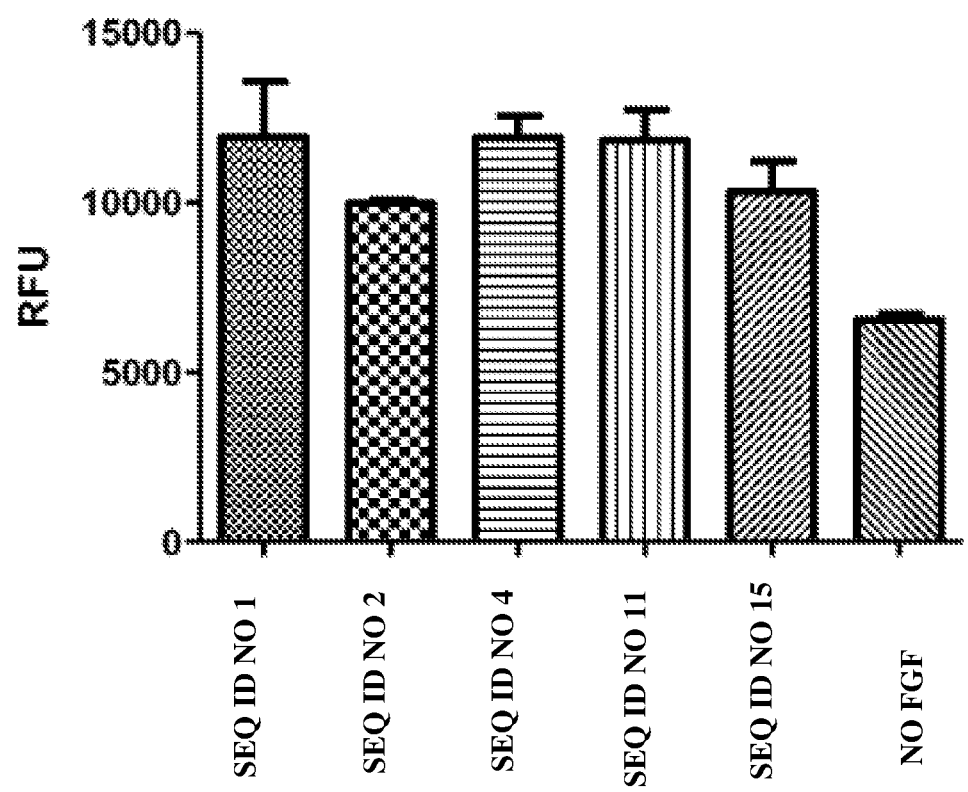
FIG. 10 illustrates stimulation of chondrocyte cell proliferation with reference polypeptides (SEQ ID NO: 1 and 2), and fusion polypeptides (SEQ ID NO: 4, SEQ ID NO: 11, and SEQ ID NO: 15).

Example 15: The Effects of FGF18 Analogues on the Growth of Human Articular Chondrocytes The fusion polypeptides of the present disclosure were tested for their ability to induce mitogenic response in chondrocytes. A representative example of the mitogenic response to the fusion polypeptides is shown in FIG. 10. As can be seen, all the fusion polypeptides tested showed an ability to stimulate chondrocyte cell proliferation comparable to that of FGF18.

Example 16: Effect on Proteoglycan Production

Figure 11:
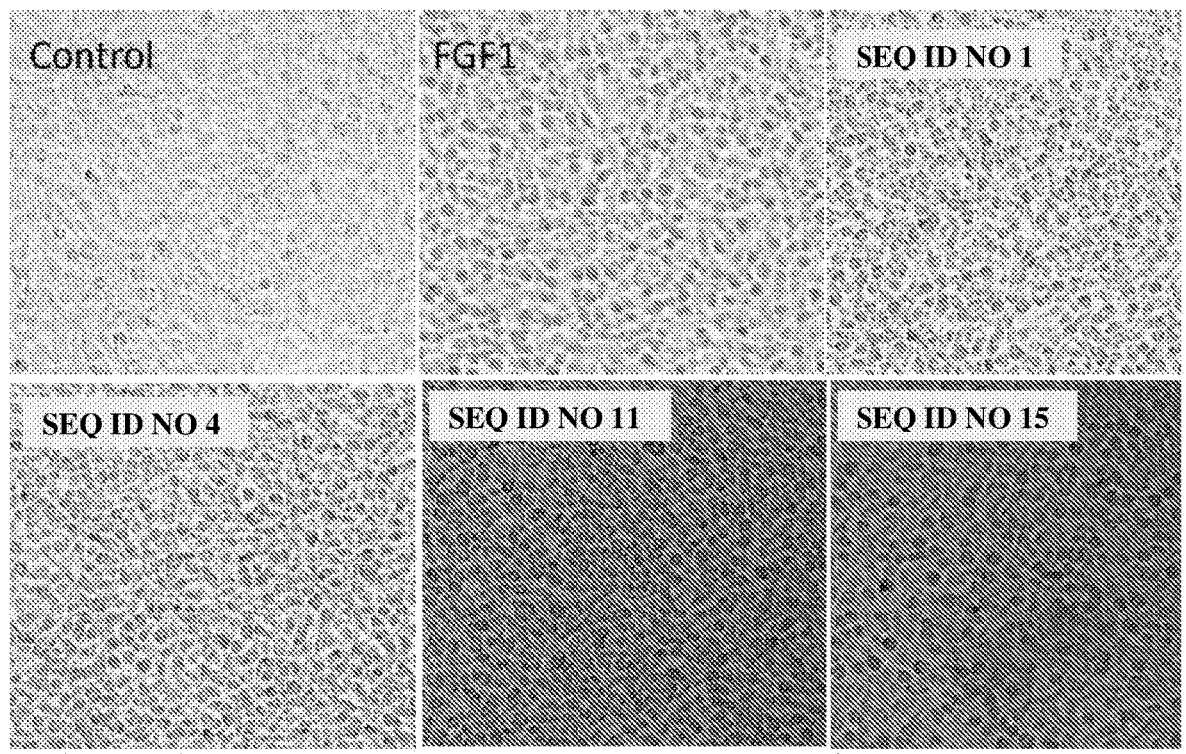
FIG. 11 illustrates the effect of reference polypeptides (SEQ ID NO: 1 and 2) and fusion polypeptides (SEQ ID NO: 4, SEQ ID NO: 11, and SEQ ID NO: 15) on proteoglycan production, as shown by Safranin 0 staining.

The effect of the fusion polypeptides on proteoglycan production was assessed on micromass cultures of human articular chondrocytes as described in Example 7. As shown in FIG. 11, the fusion polypeptides tested have an ability to increase proteoglycan synthesis comparable to that of FGF18, as revealed by Safranin 0 staining.

---

What is claimed is:

1. A fusion polypeptide comprising an amino acid sequence selected from the group consisting of SEQ ID NOs: 3 to 16.

2. The fusion polypeptide of claim 1, wherein the fusion polypeptide has an ability (i) to stimulate chondrocyte cell proliferation at a level that is comparable to that of FGF18 (SEQ ID NO: 1) or (ii) to increase proteoglycan synthesis in chondrocyte cells comparable to that of FGF18 (SEQ ID NO: 1), and wherein the fusion polypeptide comprises an amino acid sequence selected from the group consisting of SEQ ID NO: 4, 5, and 11.

3. The fusion polypeptide of claim 1, comprising an amino acid sequence selected from the group consisting of SEQ ID NO:3, SEQ ID NO:4, SEQ ID NO:5, SEQ ID NO: 6, SEQ ID NO:8, SEQ ID NO:12, SEQ ID NO:13, SEQ ID NO:14, and SEQ ID NO:15.

4. A method of treating a cartilage defect in a mammal in need thereof, the method comprising administering to said mammal a therapeutically effective amount of the fusion polypeptide of claim 1, wherein the fusion polypeptide comprises an amino acid sequence selected from the group consisting of SEQ ID NOS: 4, 11, and 15, wherein proliferation of chondrocyte cells is stimulated or proteoglycan synthesis in chondrocyte cells is increased in said mammal.

5. A pharmaceutical composition comprising at least one of the fusion polypeptides of claim 1 and a pharmaceutically acceptable excipient.

6. A fusion polypeptide comprising the amino acid sequence shown in SEQ ID NO: 11.

7. A method of treating a cartilage defect in a mammal in need thereof, the method comprising administering to said mammal a therapeutically effective amount of the fusion polypeptide of claim 6, wherein proliferation of chondrocyte cells is stimulated or proteoglycan synthesis in chondrocyte cells is increased in said mammal.

8. A pharmaceutical composition comprising the fusion polypeptide of claim 6 and a pharmaceutically acceptable excipient.

9. The fusion polypeptide of claim 1, comprising an amino acid sequence selected from the group consisting of SEQ ID NO:4 and SEQ ID NO:15.

* * * * *

SEQUENCE LISTING

<160> NUMBER OF SEQ ID NOS: 16

<210> SEQ ID NO 1
<211> LENGTH: 180
<212> TYPE: PRT
<213> ORGANISM: Homo sapiens

<400> SEQUENCE: 1

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp
    130                 135                 140
```

```
Val His Phe Met Lys Arg Tyr Pro Lys Gly Gln Pro Glu Leu Gln Lys
145                 150                 155                 160

Pro Phe Lys Tyr Thr Thr Val Thr Lys Ser Arg Arg Ile Arg Pro
                165                 170                 175

Thr His Pro Ala
            180
```

<210> SEQ ID NO 2
<211> LENGTH: 194
<212> TYPE: PRT
<213> ORGANISM: Homo sapiens

<400> SEQUENCE: 2

```
Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
                20                  25                  30

Tyr Gln Leu Tyr Ser Arg Thr Ser Gly Lys His Val Gln Val Thr Gly
            35                  40                  45

Arg Arg Ile Ser Ala Thr Ala Glu Asp Gly Asn Lys Phe Ala Lys Leu
50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Arg Arg Thr Lys Arg Thr Arg Arg Pro Gln Pro
            180                 185                 190

Leu Thr
```

<210> SEQ ID NO 3
<211> LENGTH: 189
<212> TYPE: PRT
<213> ORGANISM: Artificial Sequence
<220> FEATURE:
<223> OTHER INFORMATION: fusion polypeptide

<400> SEQUENCE: 3

```
Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Val Gln Val Thr Gly Arg Arg Ile Ser Ala
            35                  40                  45

Thr Ala Glu Asp Gly Asn Lys Phe Ala Lys Leu Ile Val Glu Thr Asp
        50                  55                  60

Thr Phe Gly Ser Arg Val Arg Ile Lys Gly Ala Glu Ser Glu Lys Tyr
```

```
                65                  70                  75                  80
Ile Cys Met Asn Lys Arg Gly Lys Leu Ile Gly Lys Pro Ser Gly Lys
                    85                  90                  95

Ser Lys Asp Cys Val Phe Thr Glu Ile Val Leu Glu Asn Asn Tyr Thr
                100                 105                 110

Ala Phe Gln Asn Ala Arg His Glu Gly Trp Phe Met Ala Phe Thr Arg
                115                 120                 125

Gln Gly Arg Pro Arg Gln Ala Ser Arg Ser Arg Gln Asn Gln Arg Glu
            130                 135                 140

Ala His Phe Ile Lys Arg Leu Tyr Gln Gly Gln Leu Pro Phe Pro Asn
145                 150                 155                 160

His Ala Glu Lys Gln Lys Gln Phe Glu Phe Val Gly Ser Ala Pro Thr
                165                 170                 175

Arg Arg Thr Lys Arg Thr Arg Arg Pro Gln Pro Leu Thr
                180                 185

<210> SEQ ID NO 4
<211> LENGTH: 189
<212> TYPE: PRT
<213> ORGANISM: Artificial Sequence
<220> FEATURE:
<223> OTHER INFORMATION: fusion polypeptide

<400> SEQUENCE: 4

Glu Glu Asn Val Asp Phe Arg Ile His Val Glu Asn Gln Thr Arg Ala
1               5                   10                  15

Arg Asp Asp Val Ser Arg Lys Gln Ile Arg Glu Tyr Gln Leu Tyr Ser
                20                  25                  30

Arg Thr Ser Gly Lys His Val Gln Val Thr Gly Arg Arg Ile Ser Ala
            35                  40                  45

Thr Ala Glu Asp Gly Asn Lys Phe Ala Lys Leu Ile Val Glu Thr Asp
50                  55                  60

Thr Phe Gly Ser Arg Val Arg Ile Lys Gly Ala Glu Ser Glu Lys Tyr
65                  70                  75                  80

Ile Cys Met Asn Lys Arg Gly Lys Leu Ile Gly Lys Pro Ser Gly Lys
                    85                  90                  95

Ser Lys Asp Cys Val Phe Thr Glu Ile Val Leu Glu Asn Asn Tyr Thr
                100                 105                 110

Ala Phe Gln Asn Ala Arg His Glu Gly Trp Phe Met Ala Phe Thr Arg
                115                 120                 125

Gln Gly Arg Pro Arg Gln Ala Ser Arg Ser Arg Gln Asn Gln Arg Glu
            130                 135                 140

Ala His Phe Ile Lys Arg Leu Tyr Gln Gly Gln Leu Pro Phe Pro Asn
145                 150                 155                 160

His Ala Glu Lys Gln Lys Gln Phe Glu Phe Val Gly Ser Ala Pro Thr
                165                 170                 175

Arg Arg Thr Lys Arg Thr Arg Arg Pro Gln Pro Leu Thr
                180                 185

<210> SEQ ID NO 5
<211> LENGTH: 185
<212> TYPE: PRT
<213> ORGANISM: Artificial Sequence
<220> FEATURE:
<223> OTHER INFORMATION: fusion polypeptide

<400> SEQUENCE: 5
```

-continued

```
Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
                20                  25                  30

Tyr Gln Leu Tyr Ser Arg Thr Ser Gly Lys His Ile Gln Val Leu Gly
            35                  40                  45

Arg Arg Ile Ser Ala Arg Gly Glu Asp Gly Asp Lys Tyr Ala Gln Leu
        50                  55                  60

Leu Val Glu Thr Asp Thr Phe Gly Ser Gln Val Arg Ile Lys Gly Lys
65                  70                  75                  80

Glu Thr Glu Phe Tyr Leu Cys Met Asn Arg Lys Gly Lys Leu Val Gly
                85                  90                  95

Lys Pro Asp Gly Thr Ser Lys Glu Cys Val Phe Ile Glu Lys Val Leu
            100                 105                 110

Glu Asn Asn Tyr Thr Ala Leu Met Ser Ala Lys Tyr Ser Gly Trp Tyr
        115                 120                 125

Val Gly Phe Thr Lys Lys Gly Arg Pro Arg Lys Gly Pro Lys Thr Arg
    130                 135                 140

Glu Asn Gln Gln Asp Val His Phe Met Lys Arg Tyr Pro Lys Gly Gln
145                 150                 155                 160

Pro Glu Leu Gln Lys Pro Phe Lys Tyr Thr Thr Val Thr Lys Arg Ser
                165                 170                 175

Arg Arg Ile Arg Pro Thr His Pro Ala
            180                 185

<210> SEQ ID NO 6
<211> LENGTH: 189
<212> TYPE: PRT
<213> ORGANISM: Artificial Sequence
<220> FEATURE:
<223> OTHER INFORMATION: fusion polypeptide

<400> SEQUENCE: 6

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Ile Gln Val Leu Gly Arg Arg Ile Ser Ala
            35                  40                  45

Arg Gly Glu Asp Gly Asp Lys Tyr Ala Gln Leu Leu Val Glu Thr Asp
        50                  55                  60

Thr Phe Gly Ser Arg Val Arg Ile Lys Gly Ala Glu Ser Glu Lys Tyr
65                  70                  75                  80

Ile Cys Met Asn Lys Arg Gly Lys Leu Ile Gly Lys Pro Ser Gly Lys
                85                  90                  95

Ser Lys Asp Cys Val Phe Thr Glu Ile Val Leu Glu Asn Asn Tyr Thr
            100                 105                 110

Ala Phe Gln Asn Ala Arg His Glu Gly Trp Phe Met Ala Phe Thr Arg
        115                 120                 125

Gln Gly Arg Pro Arg Gln Ala Ser Arg Ser Arg Gln Asn Gln Arg Glu
    130                 135                 140

Ala His Phe Ile Lys Arg Leu Tyr Gln Gly Gln Leu Pro Phe Pro Asn
145                 150                 155                 160

His Ala Glu Lys Gln Lys Gln Phe Glu Phe Val Gly Ser Ala Pro Thr
                165                 170                 175
```

Arg Arg Thr Lys Arg Thr Arg Pro Gln Pro Leu Thr
            180                 185

<210> SEQ ID NO 7
<211> LENGTH: 185
<212> TYPE: PRT
<213> ORGANISM: Artificial Sequence
<220> FEATURE:
<223> OTHER INFORMATION: fusion polypeptide

<400> SEQUENCE: 7

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Gln Val Arg Ile Lys Gly Lys
65                  70                  75                  80

Glu Thr Glu Phe Tyr Leu Cys Met Asn Arg Lys Gly Lys Leu Val Gly
                85                  90                  95

Lys Pro Asp Gly Thr Ser Lys Glu Cys Val Phe Ile Glu Lys Val Leu
            100                 105                 110

Glu Asn Asn Tyr Thr Ala Leu Met Ser Ala Lys Tyr Ser Gly Trp Tyr
        115                 120                 125

Val Gly Phe Thr Lys Lys Gly Arg Pro Arg Lys Gly Pro Lys Thr Arg
    130                 135                 140

Glu Asn Gln Gln Asp Val His Phe Met Lys Arg Tyr Pro Lys Gly Gln
145                 150                 155                 160

Pro Glu Leu Gln Lys Pro Phe Lys Tyr Thr Thr Val Thr Lys Arg Ser
                165                 170                 175

Arg Arg Ile Arg Pro Thr His Pro Ala
            180                 185

<210> SEQ ID NO 8
<211> LENGTH: 189
<212> TYPE: PRT
<213> ORGANISM: Artificial Sequence
<220> FEATURE:
<223> OTHER INFORMATION: fusion polypeptide

<400> SEQUENCE: 8

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala
        35                  40                  45

Arg Gly Glu Asp Gly Asp Lys Tyr Ala Gln Leu Leu Val Glu Thr Asp
    50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Phe Gln Asn Ala Arg His Glu Gly Trp Phe Met Ala Phe Thr Arg
            115                 120                 125

Gln Gly Arg Pro Arg Gln Ala Ser Arg Ser Arg Gln Asn Gln Arg Glu
        130                 135                 140

Ala His Phe Ile Lys Arg Leu Tyr Gln Gly Gln Leu Pro Phe Pro Asn
145                 150                 155                 160

His Ala Glu Lys Gln Lys Gln Phe Glu Phe Val Gly Ser Ala Pro Thr
                165                 170                 175

Arg Arg Thr Lys Arg Thr Arg Arg Pro Gln Pro Leu Thr
            180                 185

<210> SEQ ID NO 9
<211> LENGTH: 185
<212> TYPE: PRT
<213> ORGANISM: Artificial Sequence
<220> FEATURE:
<223> OTHER INFORMATION: fusion polypeptide

<400> SEQUENCE: 9

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
        35                  40                  45

Arg Arg Ile Ser Ala Thr Ala Glu Asp Gly Asn Lys Phe Ala Lys Leu
    50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Leu Met Ser Ala Lys Tyr Ser Gly Trp Tyr
        115                 120                 125

Val Gly Phe Thr Lys Lys Gly Arg Pro Arg Lys Gly Pro Lys Thr Arg
    130                 135                 140

Glu Asn Gln Gln Asp Val His Phe Met Lys Arg Tyr Pro Lys Gly Gln
145                 150                 155                 160

Pro Glu Leu Gln Lys Pro Phe Lys Tyr Thr Thr Val Thr Lys Arg Ser
                165                 170                 175

Arg Arg Ile Arg Pro Thr His Pro Ala
            180                 185

<210> SEQ ID NO 10
<211> LENGTH: 189
<212> TYPE: PRT
<213> ORGANISM: Artificial Sequence
<220> FEATURE:
<223> OTHER INFORMATION: fusion polypeptide

<400> SEQUENCE: 10

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Ile Gln Val Leu Gly Arg Arg Ile Ser Ala

```
            35                  40                  45
Arg Gly Glu Asp Gly Asp Lys Tyr Ala Gln Leu Leu Val Glu Thr Asp
 50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
            115                 120                 125

Lys Gly Arg Pro Arg Lys Gly Pro Lys Thr Arg Glu Asn Gln Gln Asp
            130                 135                 140

Val His Phe Met Lys Arg Leu Tyr Gln Gly Gln Leu Pro Phe Pro Asn
145                 150                 155                 160

His Ala Glu Lys Gln Lys Gln Phe Glu Phe Val Gly Ser Ala Pro Thr
                165                 170                 175

Arg Arg Thr Lys Arg Thr Arg Arg Pro Gln Pro Leu Thr
            180                 185

<210> SEQ ID NO 11
<211> LENGTH: 185
<212> TYPE: PRT
<213> ORGANISM: Artificial Sequence
<220> FEATURE:
<223> OTHER INFORMATION: fusion polypeptide

<400> SEQUENCE: 11

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Val Gln Val Thr Gly
            35                  40                  45

Arg Arg Ile Ser Ala Thr Ala Glu Asp Gly Asn Lys Phe Ala Lys Leu
 50                  55                  60

Ile Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
            115                 120                 125

Met Ala Phe Thr Arg Gln Gly Arg Pro Arg Gln Ala Ser Arg Ser Arg
            130                 135                 140

Gln Asn Gln Arg Glu Ala His Phe Ile Lys Arg Tyr Pro Lys Gly Gln
145                 150                 155                 160

Pro Glu Leu Gln Lys Pro Phe Lys Tyr Thr Thr Val Thr Lys Arg Ser
                165                 170                 175

Arg Arg Ile Arg Pro Thr His Pro Ala
            180                 185

<210> SEQ ID NO 12
<211> LENGTH: 194
<212> TYPE: PRT
```

<213> ORGANISM: Artificial Sequence
<220> FEATURE:
<223> OTHER INFORMATION: fusion polypeptide

<400> SEQUENCE: 12

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
            20                  25                  30

Tyr Gln Leu Tyr Ser Arg Thr Ser Gly Lys His Ile Gln Val Leu Gly
        35                  40                  45

Arg Arg Ile Ser Ala Arg Gly Glu Asp Gly Asp Lys Tyr Ala Gln Leu
50                  55                  60

Leu Val Glu Thr Asp Thr Phe Gly Ser Arg Val Arg Ile Lys Gly Ala
65                  70                  75                  80

Glu Ser Glu Lys Tyr Ile Cys Met Asn Lys Arg Gly Lys Leu Ile Gly
                85                  90                  95

Lys Pro Ser Gly Lys Ser Lys Asp Cys Val Phe Thr Glu Ile Val Leu
            100                 105                 110

Glu Asn Asn Tyr Thr Ala Phe Gln Asn Ala Arg His Glu Gly Trp Phe
        115                 120                 125

Met Ala Phe Thr Arg Gln Gly Arg Pro Arg Gln Ala Ser Arg Ser Arg
130                 135                 140

Gln Asn Gln Arg Glu Ala His Phe Ile Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Arg Thr Lys Arg Thr Arg Arg Pro Gln Pro
            180                 185                 190

Leu Thr

<210> SEQ ID NO 13
<211> LENGTH: 180
<212> TYPE: PRT
<213> ORGANISM: Artificial Sequence
<220> FEATURE:
<223> OTHER INFORMATION: fusion polypeptide

<400> SEQUENCE: 13

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
            20                  25                  30

Arg Thr Ser Gly Lys His Val Gln Val Thr Gly Arg Arg Ile Ser Ala
        35                  40                  45

Thr Ala Glu Asp Gly Asn Lys Phe Ala Lys Leu Ile Val Glu Thr Asp
50                  55                  60

Thr Phe Gly Ser Gln Val Arg Ile Lys Gly Lys Glu Thr Glu Phe Tyr
65                  70                  75                  80

Leu Cys Met Asn Arg Lys Gly Lys Leu Val Gly Lys Pro Asp Gly Thr
                85                  90                  95

Ser Lys Glu Cys Val Phe Ile Glu Lys Val Leu Glu Asn Asn Tyr Thr
            100                 105                 110

Ala Leu Met Ser Ala Lys Tyr Ser Gly Trp Tyr Val Gly Phe Thr Lys
        115                 120                 125

Lys Gly Arg Pro Arg Lys Gly Pro Lys Thr Arg Glu Asn Gln Gln Asp

```
                130                 135                 140
Val His Phe Met Lys Arg Tyr Pro Lys Gly Gln Pro Glu Leu Gln Lys
145                 150                 155                 160

Pro Phe Lys Tyr Thr Thr Val Thr Lys Arg Ser Arg Arg Ile Arg Pro
                165                 170                 175

Thr His Pro Ala
            180

<210> SEQ ID NO 14
<211> LENGTH: 180
<212> TYPE: PRT
<213> ORGANISM: Artificial Sequence
<220> FEATURE:
<223> OTHER INFORMATION: fusion polypeptide

<400> SEQUENCE: 14

Glu Glu Asn Val Asp Phe Arg Ile His Val Glu Asn Gln Thr Arg Ala
1               5                   10                  15

Arg Asp Asp Val Ser Arg Lys Gln Leu Arg Leu Tyr Gln Leu Tyr Ser
                20                  25                  30

Arg Thr Ser Gly Lys His Val Gln Val Thr Gly Arg Arg Ile Ser Ala
            35                  40                  45

Thr Ala Glu Asp Gly Asn Lys Phe Ala Lys Leu Ile Val Glu Thr Asp
50                  55                  60

Thr Phe Gly Ser Arg Val Arg Ile Lys Gly Ala Glu Ser Glu Lys Tyr
65                  70                  75                  80

Ile Cys Met Asn Lys Arg Gly Lys Leu Ile Gly Lys Pro Ser Gly Lys
                85                  90                  95

Ser Lys Asp Cys Val Phe Thr Glu Ile Val Leu Glu Asn Asn Tyr Thr
                100                 105                 110

Ala Phe Gln Asn Ala Arg His Glu Gly Trp Phe Met Ala Phe Thr Arg
            115                 120                 125

Gln Gly Arg Pro Arg Gln Ala Ser Arg Ser Arg Gln Asn Gln Arg Glu
        130                 135                 140

Ala His Phe Ile Lys Arg Tyr Pro Lys Gly Gln Pro Glu Leu Gln Lys
145                 150                 155                 160

Pro Phe Lys Tyr Thr Thr Val Thr Lys Arg Ser Arg Arg Ile Arg Pro
                165                 170                 175

Thr His Pro Ala
            180

<210> SEQ ID NO 15
<211> LENGTH: 180
<212> TYPE: PRT
<213> ORGANISM: Artificial Sequence
<220> FEATURE:
<223> OTHER INFORMATION: fusion polypeptide

<400> SEQUENCE: 15

Glu Glu Asn Val Asp Phe Arg Ile His Val Glu Asn Gln Thr Arg Ala
1               5                   10                  15

Arg Asp Asp Val Ser Arg Lys Gln Ile Arg Glu Tyr Gln Leu Tyr Ser
                20                  25                  30

Arg Thr Ser Gly Lys His Val Gln Val Thr Gly Arg Arg Ile Ser Ala
            35                  40                  45

Thr Ala Glu Asp Gly Asn Lys Phe Ala Lys Leu Ile Val Glu Thr Asp
50                  55                  60
```

```
Thr Phe Gly Ser Arg Val Arg Ile Lys Gly Ala Glu Ser Glu Lys Tyr
65                  70                  75                  80

Ile Cys Met Asn Lys Arg Gly Lys Leu Ile Gly Lys Pro Ser Gly Lys
                85                  90                  95

Ser Lys Asp Cys Val Phe Thr Glu Ile Val Leu Glu Asn Asn Tyr Thr
            100                 105                 110

Ala Phe Gln Asn Ala Arg His Glu Gly Trp Phe Met Ala Phe Thr Arg
        115                 120                 125

Gln Gly Arg Pro Arg Gln Ala Ser Arg Ser Arg Gln Asn Gln Arg Glu
    130                 135                 140

Ala His Phe Ile Lys Arg Tyr Pro Lys Gly Gln Pro Glu Leu Gln Lys
145                 150                 155                 160

Pro Phe Lys Tyr Thr Thr Val Thr Lys Arg Ser Arg Arg Ile Arg Pro
                165                 170                 175

Thr His Pro Ala
            180

<210> SEQ ID NO 16
<211> LENGTH: 194
<212> TYPE: PRT
<213> ORGANISM: Artificial Sequence
<220> FEATURE:
<223> OTHER INFORMATION: fusion polypeptide

<400> SEQUENCE: 16

Thr Gln Gly Glu Asn His Pro Ser Pro Asn Phe Asn Gln Tyr Val Arg
1               5                   10                  15

Asp Gln Gly Ala Met Thr Asp Gln Leu Ser Arg Arg Gln Ile Arg Glu
                20                  25                  30

Tyr Gln Leu Tyr Ser Arg Thr Ser Gly Lys His Ile Gln Val Leu Gly
            35                  40                  45

Arg Arg Ile Ser Ala Arg Gly Glu Asp Gly Asp Lys Tyr Ala Gln Leu
        50                  55                  60

Leu Val Glu Thr Asp Thr Phe Gly Ser Gln Val Arg Ile Lys Gly Lys
65                  70                  75                  80

Glu Thr Glu Phe Tyr Leu Cys Met Asn Arg Lys Gly Lys Leu Val Gly
                85                  90                  95

Lys Pro Asp Gly Thr Ser Lys Glu Cys Val Phe Ile Glu Lys Val Leu
            100                 105                 110

Glu Asn Asn Tyr Thr Ala Leu Met Ser Ala Lys Tyr Ser Gly Trp Tyr
        115                 120                 125

Val Gly Phe Thr Lys Lys Gly Arg Pro Arg Lys Gly Pro Lys Thr Arg
    130                 135                 140

Glu Asn Gln Gln Asp Val His Phe Met Lys Arg Leu Tyr Gln Gly Gln
145                 150                 155                 160

Leu Pro Phe Pro Asn His Ala Glu Lys Gln Lys Gln Phe Glu Phe Val
                165                 170                 175

Gly Ser Ala Pro Thr Arg Arg Thr Lys Arg Thr Arg Arg Pro Gln Pro
            180                 185                 190

Leu Thr
```